US008937217B2

(12) United States Patent
McGonigle

(10) Patent No.: US 8,937,217 B2
(45) Date of Patent: Jan. 20, 2015

(54) DOWN-REGULATION OF GENE EXPRESSION USING ARTIFICIAL MICRORNAS

(75) Inventor: Brian McGonigle, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 1250 days.

(21) Appl. No.: 12/335,717

(22) Filed: Dec. 16, 2008

(65) Prior Publication Data

US 2009/0155910 A1 Jun. 18, 2009

Related U.S. Application Data

(60) Provisional application No. 61/014,512, filed on Dec. 18, 2007.

(51) Int. Cl.
*C12N 15/82* (2006.01)
*A01H 5/00* (2006.01)

(52) U.S. Cl.
CPC ........ *C12N 15/8261* (2013.01); *C12N 15/8216* (2013.01); *C12N 15/8218* (2013.01)
USPC ....... 800/285; 536/24.5; 435/320.1; 435/419; 435/468

(58) Field of Classification Search
None
See application file for complete search history.

(56) References Cited

U.S. PATENT DOCUMENTS 7,786,350 B2 * 8/2010 Allen et al. .................... 800/285
2005/0138689 A1 6/2005 Aukerman

FOREIGN PATENT DOCUMENTS

| CA | 2709404 | 6/2010 |
| WO | 2004009779 | 1/2004 |
| WO | 2005/035769 A2 | 4/2005 |
| WO | 2006/073727 A2 | 7/2006 |
| WO | WO 2009/079532 | 6/2009 |

OTHER PUBLICATIONS

Bartel et al., Cell, 2004, vol. 116, pp. 281-297.*
U.S. Appl. No. 10/963,238, filed Oct. 12, 2004, E. I. du Pont de Nemours and Company.
U.S. Appl. No. 10/963,394, filed Oct. 12, 2004, E. I. du Pont de Nemours and Company.
U.S. Appl. No. 10/883,374, filed Jul. 1, 2004, Ladd et al.
U.S. Appl. No. 10/913,288, filed Aug. 6, 2004, Whitehead Institute for Biomedical Research.
U.S. Appl. No. 11/334,776, filed Jan. 6, 2006, State of OR.
Mallory et al., Nature Genetics. Functions of microRNAs and Related Small RNAs in Plants, vol. 38, p. S31-S36, 2006.
Bartel, Cell. MicroRNAs: Genomix, Biogenesis, Mechanism and Function, vol. 116, p. 281-297, 2004.
Jones-Rhoades et al., Annual Review Plant Biol. MicroRNAs and their Regulatory Roles in Plants, vol. 57, p. 19-53, 2006.
Kurihara et al., Proc Natl Acad Science. *Arabidopsis* Micro-RNA Biogenesis through Dicer-like 1 Protein Functions, vol. 101, p. 12753-12758, 2004.
Niu et al., Nature Biotechnology. Expression of Artificial MicroRNAs in Transgenic *Arabidopsis thaliana* Confers Virus Resistance, vol. 24, p. 1420-1428, 2006.
Schwab et al., Plant Cell. Highly Specific Gene Silencing by Artificial MicroRNAs in *Arabidopsis*, vol. 18, p. 1121-1133, 2006.
Parizotto et al., Genes & Development. In Vivo Investigation of the Transcription, Processing, Endonucleolytic Activity, and Functional Relevance of the Spatial Distribution of a Plant miRNA, vol. 18, p. 2237-2242, 2004.
Alvarez et al., Plant Cell. Endogenous and Synthetic MicroRNAs Stimulate Simultaneous, Efficient, and Localized Regulation of Multiple Targets in Diverse Species, vol. 18, p. 1134-1151, 2006.
Lagos-Quintana et al., Science. Identification of Novel Genes Coding for Small Expressed RNAs, vol. 294, p. 853-858, 2001.
Lagos-Quintana et al., Current Biology. Identification of Tissue-Specific MicroRNAs from Mouse, vol. 12, p. 735-739, 2002.
Lau et al., Science. An Abundant Class of Tiny RNAs with Probable Regulatory Roles in *Caenorhabditis elegans*, vol. 294, p. 858-862, 2001.
Lee et al., Science. An Extensive Class of Small RNAs in *Caenorhabditis elegans*, vol. 294, p. 862-864, 2001.
Llave et al., Plant Cell. Endogenous and Silencing-Associated Small RNAs in Plants, vol. 14, p. 1605-1619, 2002.
Mourelatos et al., Genes & Development. MiRNPs: A Novel Class of Ribonucleoproteins Containing Numerous MicroRNAs, vol. 16, p. 720-728, 2002.
Park et al., Current Biology. Carpel Factory—A Dicer Homolog, and HEN-1, a Novel Protein, Act in MicroRNA Metabolism in *Arabidopsis thaliana*, vol. 12, p. 1484-1495, 2002.
Reinhart et al., Genes & Development. MicroRNAs in Plants, vol. 16, p. 1616-1626, 2002.
Grishok et al., Cell. Genes and Mechanisms Related to RNA Interference Regulate Expression of the Small Temporal RNAs that Control *C. elegans* Developmental Timing, vol. 106, p. 23-34, 2001.
Hutvagner et al., Science. A Cellular Function for the RNA-Interference Enzyme Dicer in the Maturation of the let-7 Small Temporal RNA, vol. 293, p. 834-838, 2001.
Ketting et al., Genes & Development. Dicer Functions in RNA Interference and in Synthesis of Small RNA Involved in Developmental Timing in *C. elegans*, vol. 15, p. 2654-2659, 2001.
Schwartz et al., Cell. Asymmetry in the Assembly of the RNAi Enzyme Complex, vol. 115, p. 199-208, 2003.
Fire et al., Nature. Potent and Specific Genetic Interference by Double-Stranded RNA in *Caenorhabditis elegans*, vol. 391, p. 806-811, 1998.
Fire et al., Trends Genet. RNA-Triggered Gene Silencing, vol. 15(9), p. 358-363, 1999.
Bernstein et al., Nature. Role for a Bidentate Ribonuclease in the Initiation Step of RNA Interference, vol. 409, p. 363-366, 2001.
Elbashir et al., Genes & Development. RNA Interference is Mediated by 21- and 22-Nucleotide RNAs, vol. 15, p. 188-200, 2001.
Allshire, Science. RNAi and Heterochromatin—A Hushed-up Affair, vol. 297, p. 1818-1819, 2002.

(Continued)

*Primary Examiner* — Cynthia Collins

(57) ABSTRACT

Isolated nucleic acid fragments comprising precursor miRNAs, and artificial miRNAs and their use in down-regulating gene expression are described.

7 Claims, No Drawings

(56) References Cited

OTHER PUBLICATIONS

Volpe et al., Science. Regulation of Heterochromatic Silencing and Histone H3 Lysine-9 Methylation by RNAi, vol. 297, p. 1833-1837, 2002.
Jenuwein, Science. An RNA-Guided Pathway for the Epigenome, vol. 297, p. 2215-2218, 2002.
Hall et al., Science. Establishment and Maintenance of a Heterochromatin Domain, vol. 297, p. 2232-2237, 2002.
Wianny et al., Nature Cell Biology. Specific Interference with Gene Function by Double-Stranded RNA in Early Mouse Development, vol. 2, p. 70-75, 2000.
Hammond et al., Nature. An RNA-Directed Nuclease Mediates Post-Transcriptional Gene Silencing in *Drosophila* Cells, vol. 404, p. 293-296, 2000.
Elbashir et al., Nature. Duplexes of 21-Nucleotide RNAs Mediate RNA Interference in Cultured Mammalian Cells, vol. 411, p. 494-498, 2001.
Lee et al., Cell. The *C. elegans* Heterochronic Gene lin-4 Encodes Small RNAs with Antisense Complementarity to lin-14, vol. 75, p. 843-854, 1993.
Reinhart et al., Nature. The 21-Nucleotide let-7 RNA Regulates Developmental Timing in *Caenorhabditis elegans*, vol. 403, p. 901-906, 2000.
Wightman et al., Cell. Posttranscriptional Regulation of the Heterochronic Gene lin-14 by lin-4 Mediates Temporal Pattern Formation in *C. elegans*, vol. 75, p. 855-862, 1993.
Slack et al., Molecular Cell. The lin-41 RBCC Gene Acts in the *C. elegans* Heterochronic Pathway between the let-7 Regulatory RNA and the LIN-29 Transcription Factor, vol. 5, p. 659-669, 2000.
Olsen et al., Developmental Biology. The lin-4 Regulatory RNA Controls Developmental Timing in *Caenorhabditis elegans* by Blocking LIN-14 Protein Synthesis after the Initiation of Translation, vol. 216, p. 671-680, 1999.
Hutvagner Agner et al., Science. A Micro-RNA in a Multiple-Turnover RNAi Enzyme Complex, vol. 297, p. 2056-2060, 2002.
Rhoades et al., Cell. Prediction of Plant MicroRNA Targets, vol. 110, p. 513-520, 2002.
Schwab et al., Developmental Cell. Specific Effects of MicroRNAs on the Plant Transcriptome, vol. 8, p. 517-527, 2005.
Long et al., Nature Structural & Molecular Biology. Potent Effect of Target Structure on MicroRNA function, vol. 14, p. 287-294, 2007.
Lee et al., EMBO Journal. MicroRNA Maturation: Stepwise Processing and Subcellular Localization, vol. 21, p. 4663-4670, 2002.
Baohong Zhang et al., Identification and characterization of new plant microRNAs using EST analysis, Cell Research, May 2005, pp. 336-360, vol. 15(5).
Baohong Zhang et al., Conservation and divergence of plant microRNA genes, The Plant Journal, 2006, pp. 243-259, vol. 46.
Tobias Dezulian et al., Conservation and divergence of microRNA in plants, Genome Biology, Oct. 11, 2005, pp. 13, vol. 6.
Baohong Zhang et al., Conputational identification of microRNAs and their targets, Computational Biology and Chemistry—Elsevier, 2006, pp. 395-407, vol. 30.
Milo J. Aukerman et al., Regulation of Flowering Time and Floral organ Identity by a MicroRNA and Its Apetala2-Like Target Genes, The Plant Cell, Nov. 2003, pp. 2730-2741, vol. 15.
Tobia Dezulian et al., Identification of plant microRNA homologs, Bioinfomatics, Feb. 2006, pp. 359-360, vol. 22(3).
Rebecca Schwab et al., Specific Effects of MicroRNAs on the Plant Transcriptome, Developmental Cell, Apr. 2005, pp. 517-527, vol. 8.
Javier F. Palatnik et al., Control of leaf morphogenesis by microRNAs, Nature, Sep. 18, 2003, pp. 257-263, vol. 425.
Javier F. Palatnik et al., Sequence and Expression Differences Underlie Functional Specialization of *Arabidopsis* MicroRNAs miR159 and miR319, Developmental Cell, Jul. 2007, pp. 115-125, vol. 13.
Sam Griffiths-Jones et al., miRBase: microRNA sequences, targets and gene nomenclature, Nucleic Acids Research, 2006, pp. D140-D144, vol. 34.
Senthil Subramanian et al., Novel and nodulation-regulated microRNAs in soybean roots, BMC Genomics, Apr. 10, 2008, p. 160, vol. 9.
Baohong Zhang et al., Identification of soybean microRNAs and their targets, Planta, 2008, pp. 161-182, vol. 229.
Database Accession No. BI320499, Jul. 31, 2001.
Database Accession No. BM731193, Mar. 7, 2002.
http://wmd2.weigelworld.org, 2005.
Genbank, Database Accession No. AW459710, date created Feb. 22, 2000.
EMBL-Bank, Database Accession No. CX701995, date created Jan. 22, 2005.
Cuperus, et al., "Unique Functionality of 22-nt miRNAs in Triggering RDR6-dependent . . . ", Nature Structural & Molecular Biology, vol. 17 (8), pp. 997-1004, Aug. 2010.

\* cited by examiner

DOWN-REGULATION OF GENE EXPRESSION USING ARTIFICIAL MICRORNAS

This application claims the benefit of U.S. Provisional Application No. 61/014,512, filed Dec. 18, 2007 the disclosure of which is hereby incorporated by reference in its entirety.

FIELD OF THE INVENTION

The field of the present invention relates, generally, to plant molecular biology. In particular, it relates to constructs and methods to down-regulate expression of targeted sequences.

BACKGROUND

MicroRNAs (miRNAs) were first identified only a few years ago, but already it is clear that they play an important role in regulating gene activity. These 20-22 nucleotide non-coding RNAs have the ability to hybridize via base-pairing with specific target mRNAs and downregulate the expression of these transcripts, by mediating either RNA cleavage or translational repression.

Recent studies have indicated that miRNAs have important functions during development. In plants, they have been shown to control a variety of developmental processes including flowering time, leaf morphology, organ polarity, floral morphology, and root development (reviewed by Mallory and Vaucheret (2006) Nat Genet 38: S31-36). Given the established regulatory role of miRNAs, it is likely that they are also involved in the control of some of the major crop traits such drought tolerance and disease resistance.

miRNAs are transcribed by RNA polymerase II as polyadenylated and capped messages known as pri-miRNAs. These pri-miRNAs are processed into smaller transcripts known as pre-miRNAs and these precursors have the ability to form stable hairpin structures (reviewed by Bartel (2004) Cell 116: 281-297; Jones-Rhoades M W, Bartel D P, Bartel B. MicroRNAS and their regulatory roles in plants. Annu Rev Plant Biol. 2006;57:19-53.) While pri-miRNAs are processed to pre-miRNAs by Drosha in the nucleus and Dicer cleaves pre-miRNAs in the cytoplasm in metazoans, miRNA maturation in plants differs from the pathway in animals because plants lack a Drosha homolog. Instead, the RNase III enzyme DICER-LIKE 1 (DCL1), which is homologous to animal Dicer, may possess Drosha function in addition to its known function in hairpin processing (Kurihara and Watanabe (2004) Proc Natl Acad Sci 101: 12753-12758).

Artificial microRNAs (amiRNAs) have recently been described in *Arabidopsis* targeting viral mRNA sequences (Niu et al. (2006) *Nature Biotechnology* 24:1420-1428) or endogenous genes (Schwab et al. (2006) *Plant Cell* 18:1121-1133). The amiRNA construct can be expressed under different promoters in order to change the spatial pattern of silencing (Schwab et al. (2006) *Plant Cell* 18:1121-1133). Artificial miRNAs replace the microRNA and its complementary star sequence in a precursor miRNA and substitute sequences that target an mRNA to be silenced. Silencing by endogenous miRNAs can be found in a variety of spatial, temporal, and developmental expression patterns (Parizotto et al. (2007) *Genes Dev* 18:2237-2242; Alvarez et al. (2006) *Plant Cell* 18:1134-51). Artificial miRNA can be constructed to both capture and extend the diversity and specificity in the patterns of silencing. To date there have been no reports of using amiRNAs in crop plants.

WO 2004/009779 published Jan. 29, 2004 describes compositions and methods for modulating gene expression in plants.

Applicant's Assignee's US Patent Application Publication 2005/0138689 published on Jun. 23, 2005 describes miRNAs and their use in silencing a target sequence.

BRIEF DESCRIPTION OF THE SEQUENCE LISTING

The invention can be more fully understood from the following detailed description and the accompanying Sequence Listing, which form a part of this application.

The sequence descriptions summarize the Sequences Listing attached hereto. The Sequence Listing contains one letter codes for nucleotide sequence characters and the single and three letter codes for amino acids as defined in the IUPAC-IUB standards described in *Nucleic Acids Research* 13:3021-3030 (1985) and in the *Biochemical Journal* 219(2):345-373 (1984).

SEQ ID NOs:1-12 correspond to primers useful for amplifying soybean genomic microRNA (miRNA) precursors.

SEQ ID NOs:13-18 correspond to soybean miRNA precursor sequences for 156c, 159,166b, 168c, 396b, and 398b, respectively.

SEQ ID NO:19-21 corresponds to the artificial miRNA (amiRNA) sequence used to silence the soybean lipoxygenase (lox), fatty acid desaturase 2-1 (fad2-1), or fatty acid desaturase 2-2 (fad2-2) transcripts, respectively.

SEQ ID NOs:22-30 correspond to "star sequences" contained within amiRNA precursors for 156c-lox, 159-lox, 166b-lox, 168c-lox, 398b-lox, 159-fad2-1 b, 166b-fad2-1 b, 396b-fad2-1 b, and 159-fad2-2, respectively. Star sequences are the largely complementary sequences within the miRNA precursor that form a duplex with the miRNA.

SEQ ID NOs:31-39 correspond to amiRNA precursors for 156c-lox, 159-lox, 166b-lox, 168c-lox, 398b-lox, 159-fad2-1 b, 166b-fad2-1 b, 396b-fad2-1b, and 159-fad2-2, respectively. These precursors, when expressed in soybean, direct the silencing of the endogenous lox, fad2-1, or fad2-2 transcripts.

SEQ ID NOs:40-42 correspond to amiRNA sequence targeting fatB, a soybean thioesterase sequence, and the corresponding star sequences for the 159 and 396b precursors, respectively.

SEQ ID NOs:43-46 correspond to four versions (a-d) of amiRNA sequences targeting soybean phosphoglucomutase, respectively.

SEQ ID NOs:47-50 correspond to four star sequences for use in precursor amiRNAs targeting soybean phosphoglucomutase. Precursors containing these star sequences are 159-PGMa, 168c-PGMb, 159-PGMc, and 159-PGMd, respectively.

SUMMARY OF THE INVENTION

The present invention concerns an isolated nucleic acid fragment comprising a precursor miRNA said precursor miRNA corresponding substantially to the deoxyribonucleotide sequence set forth in SEQ ID NO:13 (i) wherein nucleotides 513 to 533 of SEQ ID NO:13 are replaced by a first variable nucleotide subsequence ranging in size from about 19 to about 30 nucleotides depending upon the target sequence whose expression is to be reduced and (ii) further wherein nucleotides 384 to 407 of SEQ ID NO:13 are replaced by a second variable nucleotide subsequence ranging in size from about 19 to about 30 nucleotides, said second variable nucleotide subsequence being capable of hybridizing to the first variable subsequence of the precursor miRNA.

Other isolated nucleic fragments which are also of interest include the following:

a) an isolated nucleic acid fragment comprising a precursor miRNA said precursor miRNA corresponding substantially to the deoxyribonucleotide sequence set forth in SEQ ID NO:14 (i) wherein nucleotides 275 to 295 SEQ ID NO:14 are replaced by a first variable nucleotide subsequence ranging in size from about 19 to about 30 nucleotides depending upon the target sequence whose expression is to be reduced and (ii) further wherein nucleotides 121 to 141 of SEQ ID NO:14 are replaced by a second variable nucleotide subsequence ranging in size from about 19 to about 30 nucleotides, said second variable nucleotide subsequence being capable of hybridizing to the first variable subsequence of the precursor miRNA;

b) an isolated nucleic acid fragment comprising a precursor miRNA said precursor miRNA corresponding substantially to the deoxyribonucleotide sequence set forth in SEQ ID NO:15 (i) wherein nucleotides 262 to 282 of SEQ ID NO:15 are replaced by a first variable nucleotide subsequence ranging in size from about 19 to about 30 nucleotides depending upon the target sequence whose expression is to be reduced and (ii) further wherein nucleotides 155 to 175 of SEQ ID NO:15 are replaced by a second variable nucleotide subsequence ranging in size from about 19 to about 30 nucleotides, said second variable nucleotide subsequence being capable of hybridizing to the first variable subsequence of the precursor miRNA;

c) an isolated nucleic acid fragment comprising a precursor miRNA said precursor miRNA corresponding substantially to the deoxyribonucleotide sequence set forth in SEQ ID NO:16 (i) wherein nucleotides 249 to 269 of SEQ ID NO:16 are replaced by a first variable nucleotide subsequence ranging in size from about 19 to about 30 nucleotides depending upon the target sequence whose expression is to be reduced and (ii) further wherein nucleotides 316 to 336 of SEQ ID NO:16 are replaced by a second variable nucleotide subsequence ranging in size from about 19 to about 30 nucleotides, said second variable nucleotide subsequence being capable of hybridizing to the first variable subsequence of the precursor miRNA;

d) an isolated nucleic acid fragment comprising a precursor miRNA said precursor miRNA corresponding substantially to the deoxyribonucleotide sequence set forth in SEQ ID NO:17 (i) wherein nucleotides 196 to 216 of SEQ ID NO:17 are replaced by a first variable nucleotide subsequence ranging in size from about 19 to about 30 nucleotides depending upon the target sequence whose expression is to be reduced and (ii) further wherein nucleotides 262 to 282 of SEQ ID NO:17 are replaced by a second variable nucleotide subsequence ranging in size from about 19 to about 30 nucleotides, said second variable nucleotide subsequence being capable of hybridizing to the first variable subsequence of the precursor miRNA; and e) an isolated nucleic acid fragment comprising a precursor miRNA said precursor miRNA corresponding substantially to the deoxyribonucleotide sequence set forth in SEQ ID NO:18 (i) wherein nucleotides 127 to 147 of SEQ ID NO:18 are replaced by a first variable nucleotide subsequence ranging in size from about 19 to about 30 nucleotides depending upon the target sequence whose expression is to be reduced and (ii) further wherein nucleotides 53 to 73 of SEQ ID NO:18 are replaced by a second variable nucleotide subsequence ranging in size from about 19 to about 30 nucleotides, said second variable nucleotide subsequence being capable of hybridizing to the first variable subsequence of the precursor miRNA.

Any of these isolated nucleic acid fragments can the be used to make a recombinant construct comprising these isolated nucleic acid fragments operably linked to at least one regulatory sequence.

These constructs can be transformed into plant cell so that the transformed plant cell comprises the recombinant construct in its genome.

In another aspect, this invention concerns a method for reducing expression of a target gene in a plant cell, said method comprising:

(a) transforming at least one plant cell with a nucleic acid construct comprising any of the isolated nucleic acid fragments described herein; and (b) selecting those transformed plant cell(s) whose level of expression of the target sequence is reduced when compared to the level of expression of the target gene in a wild type plant cell.

DETAILED DESCRIPTION

Information pertinent to this application can be found in U.S. patent application Ser. Nos. 10/963,238 (Published U.S. Patent Application No. 20050120415) and Ser. No.10/963,394 (Published U.S. Patent Application No. 20050138689), filed Oct. 12, 2004, now both abandoned. The entire contents of the above applications are herein incorporated by reference.

Other references that may be useful in understanding the invention include U.S. patent application Ser. No. 10/884,374 (Published U.S. Patent Application. No. 20050144669), filed Jul. 1, 2004, now abandoned; U.S. patent application Ser. No. 10/913,288 (Published U.S. Patent Application No. 20050075492), filed Aug. 6, 2004; and U.S. patent application Ser. No. 11/334,776 (Published U.S. Patent Application No. 20060174380), filed Jan. 6, 2006.

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

In the context of this disclosure, a number of terms and abbreviations are used. The following definitions are provided.

"microRNA or miRNA" refers to oligoribonucleic acid, which regulates expression of a polynucleotide comprising the target sequence. microRNAs (miRNAs) are noncoding RNAs of about 19 to about 24 nucleotides (nt) in length that have been identified in both animals and plants (Lagos-Quintana et al., *Science* 294:853-858 2001, Lagos-Quintana et al., *Curr. Biol.* 12:735-739 2002; Lau et al., *Science* 294:858-862 2001; Lee and Ambros, *Science* 294:862-864 2001; Llave et al., *Plant Cell* 14:1605-1619 2002; Mourelatos et al., *Genes. Dev.* 16:720-728 2002; Park et al., *Curr. Biol.* 12:1484-1495 2002; Reinhart et al., *Genes. Dev.* 16:1616-1626 2002) which regulates expression of a polynucleotide comprising the target sequence. They are processed from longer precursor transcripts that range in size from approximately 70 to 2000 nt or longer, and these precursor transcripts have the ability to form stable hairpin structures. In animals, the enzyme involved in processing miRNA precursors is called Dicer, an RNAse III-like protein (Grishok et al., *Cell* 106:23-34 2001; Hutvagner et al., *Science* 293:834-838 2001; Ketting et al., *Genes. Dev.* 15:2654-2659 2001). Plants also have a Dicer-like enzyme, DCL1 (previously named CARPEL FACTORY/SHORT INTEGUMENTS1/SUSPENSOR1), and recent evidence indicates that it, like Dicer, is involved in processing the hairpin precursors to generate mature miRNAs (Park et al., *Curr. Biol.* 12:1484-1495 2002; Reinhart et al., *Genes. Dev.* 16:1616-1626 2002). Furthermore, it is becoming clear from recent work that at least some miRNA hairpin precursors originate as longer polyadenylated transcripts, and several different miRNAs and associated hairpins can be present in a single transcript (Lagos-Quintana et al., *Science* 294:853-858 2001; Lee et al., *EMBO J* 21:4663-4670 2002). Recent work has also examined the selection of the miRNA strand from the dsRNA product arising from processing of the hairpin by DICER (Schwartz et al., 2003, *Cell* 115:199-208). It appears that the stability (i.e. G:C vs. A:U content, and/or mismatches) of the two ends of the processed dsRNA affects the strand selection, with the low stability end being easier to unwind by a helicase activity. The 5' end strand at the low stability end is incorporated into the RISC complex, while the other strand is degraded.

"pri-miRNAs" or "primary miRNAs" are long, polyadenylated RNAs transcribed by RNA polymerase II that encode miRNAs. "pre-miRNAs" are primary miRNAs that have been processed to form a shorter sequence that has the capacity to form a stable hairpin and is further processed to release a miRNA. In plants both processing steps are carried out by dicerlike and it is therefore difficult to functionally differentiate between "pri-miRNAs" and "pre-miRNAs". Therefore, a precursor miRNA, or a primary miRNA, is functionally defined herein as a nucleotide sequence that is capable of producing a miRNA. Given this functional definition, and as will be clear from the Examples and discussion herein, a precursor miRNA, primary miRNA and/or a miRNA of the invention can be represented as a ribonucleic acid or, alternatively, in a deoxyribonucleic acid form that "corresponds substantially" to the precursor miRNA, primary miRNA and/or miRNA. It is understood that the DNA in its double-stranded form will comprise a strand capable of being transcribed into the miRNA precursor described. Expression constructs, recombinant DNA constructs, and transgenic organisms incorporating the miRNA encoding DNA that results in the expression of the described miRNA precursors are described.

A "variable nucleotide subsequence" refers to a portion of a nucleotide sequence that replaces a portion of a pre-miRNA sequence provided that this subsequence is different from the sequence that is being replaced, i.e, it cannot be the same sequence.

A "target gene" refers to a gene that encodes a target RNA, ie., a gene from which a target RNA is transcribed. The gene may encode mRNA, tRNA, small RNA, etc.

A "target sequence" refers to an RNA whose expression is to be modulated, e.g., down-regulated. The target sequence may be a portion of an open reading frame, 5' or 3' untranslated region, exon(s), intron(s), flanking region, etc.

A "star sequence" is the complementary sequence within a miRNA precursor that forms a duplex with the miRNA. The complementarity of the star sequence does not need to be perfect. Non-helix disrupting substitutions (i.e. G:T base pairs etc.) are sometimes found, as well as 1-3 mismatches.

The term "genome" refers to the following: (1) the entire complement of genetic material (genes and non-coding sequences) present in each cell of an organism, or virus or organelle; (2) a complete set of chromosomes inherited as a (haploid) unit from one parent.

"Progeny" comprises any subsequent generation of a plant. Progeny will inherit, and stably segregate, genes and transgenes from its parent plant(s).

Units, prefixes, and symbols may be denoted in their SI accepted form. Unless otherwise indicated, nucleic acids are written left to right in 5' to 3' orientation; amino acid sequences are written left to right in amino to carboxyl orientation, respectively. Numeric ranges recited within the specification are inclusive of the numbers defining the range and include each integer within the defined range. Amino acids may be referred to herein by either commonly known three letter symbols or by the one-letter symbols recommended by the IUPAC-IUB Biochemical Nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms ($5^{th}$ edition, 1993). The terms defined below are more fully defined by reference to the specification as a whole.

The terms "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., *EMBO J.* 4:2411-2418 (1985); De Almeida et al., *Mol. Gen. Genetics* 218:78-86 (1989)), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others.

This construct may comprise any combination of deoxyribonucleotides, ribonucleotides, and/or modified nucleotides. The construct may be transcribed to form an RNA, wherein the RNA may be capable of forming a double-stranded RNA and/or hairpin structure. This construct may be expressed in the cell, or isolated or synthetically produced. The construct may further comprise a promoter, or other sequences which facilitate manipulation or expression of the construct.

As used here "suppression" or "silencing" or "inhibition" are used interchangeably to denote the down-regulation of the expression of a product of a target sequence relative to its normal expression level in a wild type organism. Suppression includes expression that is decreased by about 10%, 15%, 20%, 25%, 30%, 35%, 40%, 45%, 50%, 55%, 60%, 65%, 70%, 75%, 80%, 85%, 90%, 95%, or 100% relative to the wild type expression level.

As used herein, "encodes" or "encoding" refers to a DNA sequence which can be processed to generate an RNA and/or polypeptide.

As used herein, "expression" or "expressing" refers to production of a functional product, such as, the generation of an RNA transcript from an introduced construct, an endogenous DNA sequence, or a stably incorporated heterologous DNA sequence. The term may also refer to a polypeptide produced from an mRNA generated from any of the above DNA precursors. Thus, expression of a nucleic acid fragment may refer to transcription of the nucleic acid fragment (e.g., transcription resulting in mRNA or other functional RNA) and/or translation of RNA into a precursor or mature protein (polypeptide).

As used herein, "heterologous" with respect to a sequence means a sequence that originates from a foreign species, or, if from the same species, is substantially modified from its native form in composition and/or genomic locus by deliberate human intervention. For example, with respect to a nucleic acid, it can be a nucleic acid that originates from a foreign species, or is synthetically designed, or, if from the same species, is substantially modified from its native form in composition and/or genomic locus by deliberate human intervention. A heterologous protein may originate from a foreign species or, if from the same species, is substantially modified from its original form by deliberate human intervention.

The term "host cell" refers to a cell which contains or into which is introduced a nucleic acid construct and supports the replication and/or expression of the construct. Host cells may be prokaryotic cells such as E. coli, or eukaryotic cells such as fungi, yeast, insect, amphibian, nematode, or mammalian cells. Alternatively, the host cells are monocotyledonous or dicotyledonous plant cells. An example of a monocotyledonous host cell is a maize host cell.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

The term "plant parts" includes differentiated and undifferentiated tissues including, but not limited to the following: roots, stems, shoots, leaves, pollen, seeds, tumor tissue and various forms of cells and culture (e.g., single cells, protoplasts, embryos and callus tissue). The plant tissue may be in plant or in a plant organ, tissue or cell culture.

The term "plant organ" refers to plant tissue or group of tissues that constitute a morphologically and functionally distinct part of a plant.

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into ac ell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

The term "genome" as it applies to a plant cells encompasses not only chromosomal DNA found within the nucleus, but organelle DNA found within subcellular components (e.g., mitochondrial, plastid) of the cell.

The term "isolated" refers to material, such as a nucleic acid or a protein, which is: (1) substantially or essentially free from components which normally accompany or interact with the material as found in its naturally occurring environment or (2) if the material is in its natural environment, the material has been altered by deliberate human intervention to a composition and/or placed at a locus in the cell other than the locus native to the material.

As used herein, "domain" or "functional domain" refer to nucleic acid sequence(s) that are capable of eliciting a biological response in plants. The present invention concerns miRNAs composed of at least 21 nucleotide sequences acting either individually, or in concert with other miRNA sequences, therefore a domain could refer to either individual miRNAs or groups of miRNAs. Also, miRNA sequences associated with their backbone sequences could be considered domains useful for processing the miRNA into its active form. As used herein, "subdomains" or "functional subdomains" refer to subsequences of domains that are capable of eliciting a biological response in plants. A miRNA could be considered a subdomain of a backbone sequence. "Contiguous" sequences or domains refer to sequences that are sequentially linked without added nucleotides intervening between the domains. An example of a contiguous domain string is found in SEQ ID NO:7957 which represents SEQ ID NOs: 1-2652 as a continuous string that can be thought of as 2652 miRNA sequences linked together in a sequential concatenation.

RNA interference refers to the process of sequence-specific post-transcriptional gene silencing in animals mediated by short interfering RNAs (siRNAs) (Fire et al., Nature 391: 806 1998). The corresponding process in plants is commonly referred to as post-transcriptional gene silencing (PTGS) or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire et al., Trends Genet. 15:358 1999). Such protection from foreign gene expression may have evolved in response to the production of double-stranded RNAs (dsRNAs) derived from viral infection or from the random integration of transposon elements into a host genome via a cellular response that specifically destroys homologous single-stranded RNA of viral genomic RNA. The presence of dsRNA in cells triggers the RNAi response through a mechanism that has yet to be fully characterized.

The presence of long dsRNAs in cells stimulates the activity of a ribonuclease III enzyme referred to as "dicer". Dicer is involved in the processing of the dsRNA into short pieces of dsRNA known as short interfering RNAs (siRNAs) (Berstein et al., Nature 409:363 2001) and/or pre miRNAs into miRNAs. Short interfering RNAs derived from dicer activity are typically about 21 to about 23 nucleotides in length and comprise about 19 base pair duplexes (Elbashir et al., Genes Dev. 15:188 2001). Dicer has also been implicated in the excision of 21- and 22-nucleotide small temporal RNAs (stRNAs) from precursor RNA of conserved structure that are implicated in translational control (Hutvagner et al., 2001, Science 293:834). The RNAi response also features an endonuclease complex, commonly referred to as an RNA-induced silencing complex (RISC), which mediates cleavage of single-stranded RNA having sequence complementarity to the antisense strand of the siRNA duplex. Cleavage of the target RNA takes place in the middle of the region complementary to the antisense strand of the siRNA duplex (Elbashir et al., Genes Dev. 15:188 2001). In addition, RNA interference can also involve small RNA (e.g., microRNA, or miRNA) mediated gene silencing, presumably through cellular mechanisms that regulate chromatin structure and thereby prevent transcription of target gene sequences (see, e.g., Allshire, *Science* 297:1818-1819 2002; Volpe et al., *Science* 297:1833-1837 2002; Jenuwein, *Science* 297:2215-2218 2002; and Hall et al., *Science* 297:2232-2237 2002). As such, miRNA molecules of the invention can be used to mediate gene silencing via interaction with RNA transcripts or alternately by interaction with particular gene sequences, wherein such interaction results in gene silencing either at the transcriptional or post-transcriptional level.

RNAi has been studied in a variety of systems. Fire et al. (*Nature* 391:806 1998) were the first to observe RNAi in *C. elegans*. Wianny and Goetz (*Nature Cell Biol.* 2:70 1999) describe RNAi mediated by dsRNA in mouse embryos. Hammond et al. (*Nature* 404:293 2000) describe RNAi in *Drosophila* cells transfected with dsRNA. Elbashir et al., (*Nature* 411:494 2001) describe RNAi induced by introduction of duplexes of synthetic 21-nucleotide RNAs in cultured mammalian cells including human embryonic kidney and HeLa cells.

Small RNAs play an important role in controlling gene expression. Regulation of many developmental processes, including flowering, is controlled by small RNAs. It is now possible to engineer changes in gene expression of plant genes by using transgenic constructs which produce small RNAs in the plant.

Small RNAs appear to function by base-pairing to complementary RNA or DNA target sequences. When bound to RNA, small RNAs trigger either RNA cleavage or translational inhibition of the target sequence. When bound to DNA target sequences, it is thought that small RNAs can mediate DNA methylation of the target sequence. The consequence of these events, regardless of the specific mechanism, is that gene expression is inhibited.

MicroRNAs (miRNAs) are noncoding RNAs of about 19 to about 24 nucleotides (nt) in length that have been identified in both animals and plants (Lagos-Quintana et al., *Science* 294:853-858 2001, Lagos-Quintana et al., *Curr. Biol.* 12:735-739 2002; Lau et al., *Science* 294:858-862 2001; Lee and Ambros, *Science* 294:862-864 2001; Llave et al., *Plant Cell* 14:1605-1619 2002; Mourelatos et al., *Genes. Dev.* 16:720-728 2002; Park et al., *Curr. Biol.* 12:1484-1495 2002; Reinhart et al., *Genes. Dev.* 16:1616-1626 2002). They are processed from longer precursor transcripts that range in size from approximately 70 to 200 nt, and these precursor transcripts have the ability to form stable hairpin structures. In animals, the enzyme involved in processing miRNA precursors is called Dicer, an RNAse III-like protein (Grishok et al., *Cell* 106:23-34 2001; Hutvagner et al., *Science* 293:834-838 2001; Ketting et al., *Genes. Dev.* 15:2654-2659 2001). Plants also have a Dicer-like enzyme, DCL1 (previously named CARPEL FACTORY/SHORT INTEGUMENTS1/SUSPENSOR1), and recent evidence indicates that it, like Dicer, is involved in processing the hairpin precursors to generate mature miRNAs (Park et al., *Curr. Biol.* 12:1484-1495 2002; Reinhart et al., *Genes. Dev.* 16:1616-1626 2002). Furthermore, it is becoming clear from recent work that at least some miRNA hairpin precursors originate as longer polyadenylated transcripts, and several different miRNAs and associated hairpins can be present in a single transcript (Lagos-Quintana et al., *Science* 294:853-858 2001; Lee et al., *EMBO J* 21:4663-4670 2002). Recent work has also examined the selection of the miRNA strand from the dsRNA product arising from processing of the hairpin by DICER (Schwartz et al., 2003, Cell 115:199-208). It appears that the stability (i.e. G:C vs. A:U content, and/or mismatches) of the two ends of the processed dsRNA affects the strand selection, with the low stability end being easier to unwind by a helicase activity. The 5' end strand at the low stability end is incorporated into the RISC complex, while the other strand is degraded.

In animals, there is direct evidence indicating a role for specific miRNAs in development. The lin-4 and let-7 miRNAs in *C. elegans* have been found to control temporal development, based on the phenotypes generated when the genes producing the lin-4 and let-7 miRNAs are mutated (Lee et al., *Cell* 75:843-854 1993; Reinhart et al., *Nature* 403-901-906 2000). In addition, both miRNAs display a temporal expression pattern consistent with their roles in developmental timing. Other animal miRNAs display developmentally regulated patterns of expression, both temporal and tissue-specific (Lagos-Quintana et al., *Science* 294:853-853 2001, Lagos-Quintana et al., *Curr. Biol.* 12:735-739 2002; Lau et al., *Science* 294:858-862 2001; Lee and Ambros, *Science* 294:862-864 2001), leading to the hypothesis that miRNAs may, in many cases, be involved in the regulation of important developmental processes. Likewise, in plants, the differential expression patterns of many miRNAs suggests a role in development (Llave et al., *Plant Cell* 14:1605-1619 2002; Park et al., *Curr. Biol.* 12:1484-1495 2002; Reinhart et al., *Genes. Dev.* 16:1616-1626 2002). However, a developmental role for miRNAs has not been directly proven in plants, because to date there has been no report of a developmental phenotype associated with a specific plant miRNA.

MicroRNAs appear to regulate target genes by binding to complementary sequences located in the transcripts produced by these genes. In the case of lin-4 and let-7, the target sites are located in the 3' UTRs of the target mRNAs (Lee et al., *Cell* 75:843-854 1993; Wightman et al., *Cell* 75:855-862 1993; Reinhart et al., *Nature* 403:901-906 2000; Slack et al., *Mol. Cell* 5:659-669 2000), and there are several mismatches between the lin-4 and let-7 miRNAs and their target sites. Binding of the lin-4 or let-7 miRNA appears to cause downregulation of steady-state levels of the protein encoded by the target mRNA without affecting the transcript itself (Olsen and Ambros, *Dev. Biol.* 216:671-680 1999). On the other hand, recent evidence suggests that miRNAs can, in some cases, cause specific RNA cleavage of the target transcript within the target site (Hutvagner and Zamore, *Science* 297: 2056-2060 2002; Llave et al., *Plant Cell* 14:1605-1619 2002). It seems likely that miRNAs can enter at least two pathways of target gene regulation: Protein downregulation and RNA cleavage. MicroRNAs entering the RNA cleavage pathway incorporated into an RNA-induced silencing complex (RISC) that is similar or identical to that seen for RNAi.

The present invention concerns an isolated nucleic acid fragment comprising a precursor miRNA said precursor miRNA corresponding substantially to the deoxyribonucleotide sequence set forth in SEQ ID NO:13 (i) wherein nucleotides 513 to 533 of SEQ ID NO:13 are replaced by a first variable nucleotide subsequence ranging in size from about 19 to about 30 nucleotides depending upon the target sequence whose expression is to be reduced and (ii) further wherein nucleotides 384 to 407 of SEQ ID NO:13 are replaced by a second variable nucleotide subsequence ranging in size from about 19 to about 30 nucleotides, said second variable nucleotide subsequence being capable of hybridizing to the first variable subsequence of the precursor miRNA.

This isolated nucleic acid fragment comprising a precursor miRNA may be also be referred to as a "miRNA backbone". It is well known by those skilled in the art that it is difficult to differentiate if a transcript is a full-length pri-miRNA or a pre-miRNA. Therefore, a precursor miRNA is functionally defined as a nucleotide sequence that is capable of producing a miRNA.

Other isolated nucleic fragments of interest include the following;

a) transcribed froman isolated nucleic acid fragment comprising a precursor miRNA said precursor miRNA corresponding substantially to the deoxyribonucleotide sequence set forth in SEQ ID NO:14 (i) wherein nucleotides 275 to 295 SEQ ID NO:14 are replaced by a first variable nucleotide subsequence ranging in size from about 19 to about 30 nucleotides depending upon the target sequence whose expression is to be reduced and (ii) further wherein nucleotides 121 to 141 of SEQ ID NO:14 are replaced by a second variable nucleotide subsequence ranging in size from about 19 to about 30 nucleotides, said second variable nucleotide subsequence being capable of hybridizing to the first variable subsequence of the precursor miRNA;

b) an isolated nucleic acid fragment comprising a precursor miRNA said precursor miRNA corresponding substantially to the deoxyribonucleotide sequence set forth in SEQ ID NO:15 (i) wherein nucleotides 262 to 282 of SEQ ID NO:15 are replaced by a first variable nucleotide subsequence ranging in size from about 19 to about 30 nucleotides depending upon the target sequence whose expression is to be reduced and (ii) further wherein nucleotides 155 to 175 of SEQ ID NO:15 are replaced by a second variable nucleotide subsequence ranging in size from about 19 to about 30 nucleotides, said second variable nucleotide subsequence being capable of hybridizing to the first variable subsequence of the precursor miRNA;

c) an isolated nucleic acid fragment comprising a precursor miRNA said precursor miRNA corresponding substantially to the deoxyribonucleotide sequence set forth in SEQ ID NO:16 (i) wherein nucleotides 249 to 269 of SEQ ID NO:16 are replaced by a first variable nucleotide subsequence ranging in size from about 19 to about 30 nucleotides depending upon the target sequence whose expression is to be reduced and (ii) further wherein nucleotides 316 to 336 of SEQ ID NO:16 are replaced by a second variable nucleotide subsequence ranging in size from about 19 to about 30 nucleotides, said second variable nucleotide subsequence being capable of hybridizing to the first variable subsequence of the precursor miRNA;

d) an isolated nucleic acid fragment comprising a precursor miRNA said precursor miRNA corresponding substantially to the deoxyribonucleotide sequence set forth in SEQ ID NO:17 (i)wherein nucleotides 196 to 216 of SEQ ID NO:17 are replaced by a first variable nucleotide subsequence ranging in size from about 19 to about 30 nucleotides depending upon the target sequence whose expression is to be reduced and (ii) further wherein nucleotides 262 to 282 of SEQ ID NO:17 are replaced by a second variable nucleotide subsequence ranging in size from about 19 to about 30 nucleotides, said second variable nucleotide subsequence being capable of hybridizing to the first variable subsequence of the precursor miRNA; and e) an isolated nucleic acid fragment comprising a precursor miRNA said precursor miRNA corresponding substantially to the deoxyribonucleotide sequence set forth in SEQ ID NO:18 (i) wherein nucleotides 127 to 147 of SEQ ID NO:18 are replaced by a first variable nucleotide subsequence ranging in size from about 19 to about 30 nucleotides depending upon the target sequence whose expression is to be reduced and (ii) further wherein nucleotides 53 to 73 of SEQ ID NO:18 are replaced by a second variable nucleotide subsequence ranging in size from about 19 to about 30 nucleotides, said second variable nucleotide subsequence being capable of hybridizing to the first variable subsequence of the precursor miRNA.

Any of these isolated nucleic acid fragments can the be used to make a recombinant construct comprising these isolated nucleic acid fragments operably linked to at least one regulatory sequence. These constructs can be transformed into plant cells so that the transformed plant cell comprises the recombinant construct in its genome. Preferably, the plant cell can be a dicot plant cell. Examples of dicot plant cells include, but are not limited to, soybean, rapeseed, sunflower, flax, cotton, alfalfa, barley, bean, pea, tobacco, and *Arabidopsis*.

The most preferred dicot plant cell is soybean.

In another aspect, this invention concerns a method for reducing expression of a target sequence in a plant cell, said method comprising:

(a) transforming at least one plant cell with a nucleic acid construct comprising a comprising any of the isolated nucleic acid fragments described herein; and (b) selecting those transformed plant cell(s) whose level of expression of the target sequence is reduced when compared to the level of expression of the target sequence in a wild type plant cell.

Bioinformatic approaches have been successfully used to predict targets for plant miRNAs (Llave et al., *Plant Cell* 14:1605-1619 2002; Park et al., *Curr. Biol.* 12:1484-1495 2002; Rhoades et al., *Cell* 110:513-520 2002), and thus it appears that plant miRNAs have higher overall complementarity with their putative targets than do animal miRNAs. Most of these predicted target transcripts of plant miRNAs encode members of transcription factor families implicated in plant developmental patterning or cell differentiation.

General categories of sequences of interest include, for example, those genes involved in regulation or information, such as zinc fingers, transcription factors, homeotic genes, or cell cycle and cell death modulators, those involved in communication, such as kinases, and those involved in housekeeping, such as heat shock proteins.

Target sequences may include coding regions and non-coding regions such as promoters, enhancers, terminators, introns and the like.

The target sequence may be an endogenous sequence, or may be an introduced heterologous sequence, or transgene. For example, the methods may be used to alter the regulation or expression of a transgene, or to remove a transgene or other introduced sequence such as an introduced site-specific recombination site. The target sequence may also be a sequence from a pathogen, for example, the target sequence may be from a plant pathogen such as a virus, a mold or fungus, an insect, or a nematode. A miRNA could be expressed in a plant which, upon infection or infestation, would target the pathogen and confer some degree of resistance to the plant.

In plants, other categories of target sequences include genes affecting agronomic traits, insect resistance, disease resistance, herbicide resistance, sterility, grain characteristics, and commercial products. Genes of interest also included those involved in oil, starch, carbohydrate, or nutrient metabolism as well as those affecting, for example, kernel size, sucrose loading, and the like. The quality of grain is reflected in traits such as levels and types of oils, saturated and unsaturated, quality and quantity of essential amino acids, and levels of cellulose. For example, genes of the phytic acid biosynthetic pathway could be suppressed to generate a high available phosphorous phenotype. See, for example, phytic acid biosynthetic enzymes including inositol polyphosphate kinase-2 polynucleotides, disclosed in WO 02/059324, inositol 1,3,4-trisphosphate 5/6-kinase polynucleotides, disclosed in WO 03/027243, and myo-inositol 1-phosphate synthase and other phytate biosynthetic polynucleotides, disclosed in WO 99/05298, all of which are herein incorporated by reference. Genes in the lignification pathway could be suppressed to enhance digestibility or energy availability. Genes affecting cell cycle or cell death could be suppressed to affect growth or stress response. Genes affecting DNA repair and/or recombination could be suppressed to increase genetic variability. Genes affecting flowering time could be suppressed, as well as genes affecting fertility. Any target sequence could be suppressed in order to evaluate or confirm its role in a particular trait or phenotype, or to dissect a molecular, regulatory, biochemical, or proteomic pathway or network.

A number of promoters can be used. These promoters can be selected based on the desired outcome. It is recognized that different applications will be enhanced by the use of different promoters in plant expression cassettes to modulate the timing, location and/or level of expression of the miRNA. Such plant expression cassettes may also contain, if desired, a promoter regulatory region (e.g., one conferring inducible, constitutive, environmentally- or developmentally-regulated, or cell- or tissue-specific/selective expression), a transcription initiation start site, a ribosome binding site, an RNA processing signal, a transcription termination site, and/or a polyadenylation signal.

Constitutive, tissue-preferred or inducible promoters can be employed. Examples of constitutive promoters include the cauliflower mosaic virus (CaMV) 35S transcription initiation region, the 1'- or 2'-promoter derived from T-DNA of *Agrobacterium tumefaciens*, the ubiquitin 1 promoter, the Smas promoter, the cinnamyl alcohol dehydrogenase promoter (U.S. Pat. No. 5,683,439), the Nos promoter, the pEmu promoter, the rubisco promoter, the GRP1-8 promoter and other transcription initiation regions from various plant genes known to those of skill. If low level expression is desired, weak promoter(s) may be used. Weak constitutive promoters include, for example, the core promoter of the Rsyn7 promoter (WO 99/43838 and U.S. Pat. No. 6,072,050), the core 35S CaMV promoter, and the like. Other constitutive promoters include, for example, U.S. Pat. Nos. 5,608,149; 5,608,144; 5,604,121; 5,569,597; 5,466,785; 5,399,680; 5,268,463; and 5,608,142. See also, U.S. Pat. No. 6,177,611, herein incorporated by reference.

Examples of inducible promoters are the Adh1 promoter which is inducible by hypoxia or cold stress, the Hsp70 promoter which is inducible by heat stress, the PPDK promoter and the pepcarboxylase promoter which are both inducible by light. Also useful are promoters which are chemically inducible, such as the In2-2 promoter which is safener induced (U.S. Pat. No. 5,364,780), the ERE promoter which is estrogen induced, and the Axig1 promoter which is auxin induced and tapetum specific but also active in callus (PCT US01/22169).

Examples of promoters under developmental control include promoters that initiate transcription preferentially in certain tissues, such as leaves, roots, fruit, seeds, or flowers. An exemplary promoter is the anther specific promoter 5126 (U.S. Pat. Nos. 5,689,049 and 5,689,051). Examples of seed-preferred promoters include, but are not limited to, 27 kD gamma zein promoter and waxy promoter, Boronat, A. et al. (1986) *Plant Sci.* 47:95-102; Reina, M. et al. *Nucl. Acids Res.* 18(21):6426; and Kloesgen, R. B. et al. (1986) *Mol. Gen. Genet.* 203:237-244. Promoters that express in the embryo, pericarp, and endosperm are disclosed in U.S. Pat. No. 6,225,529 and PCT publication WO 00/12733. The disclosures each of these are incorporated herein by reference in their entirety.

In some embodiments it will be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819, herein incorporated by reference.

Of interest are promoters that are expressed locally at or near the site of pathogen infection. See, for example, Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189-200).

Additionally, as pathogens find entry into plants through wounds or insect damage, a wound-inducible promoter may be used in the constructions of the polynucleotides. Such wound-inducible promoters include potato proteinase inhibitor (pin II) gene (Ryan (1990) *Ann. Rev. Phytopath.* 28:425-449; Duan et al. (1996) *Nature Biotech.* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Lett.* 323:73-76); MPI gene (Corderok et al. (1994) *Plant J.* 6(2):141-150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced expression of a sequence of interest within a particular plant tissue. Tissue-preferred promoters include Yamamoto et al. (1997) *Plant J.* 12(2):255-265; Kawamata et al. (1997) *Plant Cell Physiol.* 38(7):792-803; Hansen et al.

(1997) *Mol. Gen Genet.* 254(3):337-343; Russell et al. (1997) *Transgenic Res.* 6(2):157-168; Rinehart et al. (1996) *Plant Physiol.* 11 2(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6): 1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590. In addition, the promoters of cab and rubisco can also be used. See, for example, Simpson et al. (1958) *EMBO J* 4:2723-2729 and Timko et al. (1988) *Nature* 318:57-58. Root-preferred promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of Agrobacterium tumefaciens); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2):343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and rolB promoter (Capana et al. (1994) *Plant Mol. Biol.* 25(4): 681-691. See also U.S. Pat. Nos. 5,837,876; 5,750,386; 5,633,363; 5,459,252; 5,401,836; 5,110,732; and 5,023,179. The phaseolin gene (Murai et al. (1983) *Science* 23:476-482 and Sengopta-Gopalen et al. (1988) *PNAS* 82:3320-3324.

Transformation protocols as well as protocols for introducing nucleotide sequences into plants may vary depending on the type of plant or plant cell, i.e., monocot or dicot, targeted for transformation. Suitable methods of introducing the DNA construct include microinjection (Crossway et al. (1986) *Biotechniques* 4:320-334; and U.S. Pat. No. 6,300,543), sexual crossing, electroporation (Riggs et al. (1986) *Proc. Natl. Acad. Sci. USA* 83:5602-5606), *Agrobacterium*-mediated transformation (Townsend et al., U.S. Pat No. 5,563,055; and U.S. Pat. No. 5,981,840), direct gene transfer (Paszkowski et al. (1984) *EMBO J.* 3:2717-2722), and ballistic particle acceleration (see, for example, Sanford et al., U.S. Pat. No. 4,945, 050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923-926). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Tomes, U.S. Pat. No. 5,240,855; Buising et al., U.S. Pat. Nos. 5,322,783 and 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; Bowen et al., U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, New York), pp.197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); and U.S. Pat. No. 5,736,369 (meristem transformation), all of which are herein incorporated by reference.

The nucleotide constructs may be introduced into plants by contacting plants with a virus or viral nucleic acids. Generally, such methods involve incorporating a nucleotide construct of the invention within a viral DNA or RNA molecule. Further, it is recognized that useful promoters encompass promoters utilized for transcription by viral RNA polymerases. Methods for introducing nucleotide constructs into plants and expressing a protein encoded therein, involving viral DNA or RNA molecules, are known in the art. See, for example, U.S. Pat. Nos. 5,889,191, 5,889,190, 5,866,785, 5,589,367 and 5,316,931; herein incorporated by reference.

In some embodiments, transient expression may be desired. In those cases, standard transient transformation techniques may be used. Such methods include, but are not limited to viral transformation methods, and microinjection of DNA or RNA, as well other methods well known in the art.

The cells from the plants that have stably incorporated the nucleotide sequence may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic imparted by the nucleotide sequence of interest and/or the genetic markers contained within the target site or transfer cassette. Two or more generations may be grown to ensure that expression of the desired phenotypic characteristic is stably maintained and inherited and then seeds harvested to ensure expression of the desired phenotypic characteristic has been achieved.

Lipoxygenases are dioxygenases that catalyze, as a primary reaction, the hydroperoxidation, by molecular oxygen, of linoleic acid (18:2) and any other polyunsaturated lipids that contain a cis, cis-1,4-pentadiene moiety. Lipoxygenases (also referred to as LOX) are membrane-associated ubiquitous enzymes that catalyze the first step of a fatty acid metabolism pathway. Products of this pathway are found as signal molecules, involved in growth and development regulation, in senescence, and in response to pathogen invasion and wound stress (Rosahl (1996) Z. Naturforsch. (C) 51:123 138). Lipoxygenases with different specificities, subcellular location, and tissue-specific expression patterns have been identified in several plants including rice, barley, soybean, tomato, cucumber and potato.

Soybean seeds contain high levels of lipoxygenase. Three seed-expressed isozymes, designated lipoxygenases 1, 2 and 3 (also referred to as LOX1, LOX2, and LOX3), have been identified and well characterized enzymatically. The genes encoding the three soybean seed isozymes have been cloned and sequenced. However, no clear physiological role has yet been attributed to the soybean seed lipoxygenases (Siedow (1991) Annu. Rev. Plant Physiol. Plant Mol. Biol. 42:145-188).

EXAMPLES

Example 1

Isolation of Genomic MicroRNA Precursor Genes

Sequences encoding portions of soybean microRNA precursors found in the miRBase (miRBase: microRNA sequences, targets and gene nomenclature. Griffiths-Jones S, Grocock R J, van Dongen S, Bateman A, Enright A J. NAR, 2006, 34, Database Issue, D140-D144; The microRNA Registry. Griffiths-Jones S. NAR, 2004, 32, Database Issue, D109-D111; Dezulian T, Palatnik J F, Huson D H, Weigel D (2005) Conservation and divergence of microRNA families in plants) were used as queries for BLAST analysis of the Pioneer Unisoy 3.0 collection of expressed sequence tags. The following primers (purchased from MWG-BIOTECH Inc.) were designed to amplify a selection of six of these sequences (see Table 1).

All primers with an "A" suffix (SEQ ID Nos: 1, 3, 5, 7, 9, 11) included nucleotides that encoded a Kpn I (GGTACC) and an Xho I (CTCGAG) site. All primers with an "S" suffix (SEQ ID Nos: 2, 4, 6, 8, 10, 12) included nucleotides that encoded a Bam Hi (GGATCC) and an Nco I (CCATGG) site.

Glycine max cv. Jack seeds were grown in a growth chamber and genomic DNA was made from leaf tissue using the Qiagen DNeasy Plant Maxi Kit according to the manufacture's instructions. DNA products were amplified using the genomic DNA as template and primers pairs above with ExTaq polymerase (TaKaRa Bio Inc.). The resulting DNA products were cloned into pCR2.1 (Invitrogen) and completely sequenced. The characterized microRNA precursors are summarized in Table 2.

TABLE 2

MicroRNA Precursor Sequences

| microRNA Precursor | SEQ ID NO | Length (nucs) |
|---|---|---|
| 156c | 13 | 847 |
| 159 | 14 | 958 |
| 166b | 15 | 394 |
| 168c | 16 | 1068 |
| 396b | 17 | 574 |
| 398b | 18 | 463 |

Example 2

Design of Artificial MicroRNA sequences

Artificial microRNAs (amiRNAs) that would have the ability to silence the desired target genes were designed largely according to rules described in Schwab R, et al. (2005) *Dev Cell* 8: 517-27. To summarize, microRNA sequences are 21 nucleotides in length, start at their 5'-end with a "U", display 5' instability relative to their star sequence which is achieved by including a C or G at position 19, and their 10th nucleotide is either an "A" or an "U". An additional requirement for artificial microRNA design was that the amiRNA have a high

TABLE 1

Primers For Amplification of Genomic MicroRNA Precursors

| Primer | Primer Sequence | SEQ ID NO | direction |
|---|---|---|---|
| 156cA | 5'-ggtacctcgagtttcatcaaagaaaataacttctgaac-3' | 1 | sense |
| 156cS | 5'-ggatccatggtagaatcntacactttggtagccctg-3' | 2 | antisense |
| 159A | 5'-ggtacctcgagttctagctagctagggtttgggtag-3' | 3 | sense |
| 159S | 5'-ggatccatggagatttgtttataaaaatccaacaatc-3' | 4 | antisense |
| 166bA | 5'-ggtacctcgaggtgcagattgagagaaagatgaaag-3' | 5 | antisense |
| 166bS | 5'-ggatccatgggggaactataaggcttcggaccagg-3' | 6 | sense |
| 168cA | 5'-ggtacctcgaggtgctctttataaataaccctcg-3' | 7 | sense |
| 168cS | 5'-ggatccatggaattactttgacatagtagtatgc-3' | 8 | antisense |
| 396bA | 5'-ggtacctcgagcttatatataacaaagccataaatc-3' | 9 | antisense |
| 396bS | 5'-ggatccatgggcgagaaactttgtatgggcatgg-3' | 10 | sense |
| 398bA | 5'-ggtacctcgagtatatttccacaatgatgttattcttac-3' | 11 | antisense |
| 398bS | 5'-ggatccatgggttttgctcattcaaatgttcttcctag-3' | 12 | sense | free delta-G as calculated using the ZipFold algorithm (Markham, N. R. & Zuker, M. (2005) *Nucleic Acids Res.* 33: W577-W581.) Optionally, a one base pair change was added within the 5' portion of the amiRNA so that the sequence differed from the target sequence by one nucleotide. The amiRNA that was used to silence the lipoxygenase was 5'-ucaucagucauccauggagac-3' (SEQ ID NO:19). The amiRNA that was used to silence fad2-1 was 5'-ugagggaaaaggguugaggaa-3' (the DNA sequence corresponding to this amiRNA is represented by SEQ ID NO:20). The amiRNA that was used to silence the fad2-2 was 5'-uccacauaaauacacucucuu-3' (the DNA sequence corresponding to this amiRNA is represented by SEQ ID NO:21).

Example 3

Design of an Artificial Star Sequences

"Star sequences" are those that base pair with the amiRNA sequences, in the precursor RNA, to form imperfect stem structures. To form a perfect stem structure the star sequence would be the exact reverse complement of the amiRNA. The maize precursor sequence as described by Zhang et al. in Supplemental material Table S1 was folded using mfold (M. Zuker (2003) *Nucleic Acids Res.* 31: 3406-15; and D. H. Mathews, J. et al. (1999) *J. Mol. Biol.* 288: 911-940). The miRNA sequence was then replaced with the amiRNA sequence and the endogenous star sequence was replaced with the exact reverse complement of the amiRNA. Changes in the artificial star sequence were introduced so that the structure of the stem would remain the same as the endogenous structure. The altered sequence was then folded with mfold and the original and altered structures were compared by eye. If necessary, further alternations to the artificial star sequence were introduced to maintain the original structure. The DNA sequences corresponding to the artificial star sequences that were used to silence the desired target genes are shown in Table 3.

TABLE 3

Artificial microRNA Star Sequences

| amiRNA precursor | Star Sequence | SEQ ID NO |
|---|---|---|
| 156c-lox | 5'-caatccctgttcgactgtaca-3' | 22 |
| 159-lox | 5'-gtctccatggagaactgatgt-3' | 23 |
| 166b-lox | 5'-cactccatttatgactcttga-3' | 24 |
| 168c-lox | 5'-ctctccctggatgactgttga-3' | 25 |
| 398b-lox | 5'-gtcgccagtggatgactgatga-3' | 26 |
| 159-fad2-1b | 5'-ttcctcaacccaattccctct-3' | 27 |
| 166b-fad2-1b | 5'-cccctcaaggcttttcaatca-3' | 28 |
| 396b-fad2-1b | 5'-ttactcaaccctttccctca-3' | 29 |
| 159-fad2-2 | 5'-aagagagtgtacctatgtggt-3' | 30 |

Example 4

Conversion of Genomic MicroRNA Precursors to Artificial MicroRNA Precursors

Genomic miRNA precursor genes can be converted to amiRNAs using overlapping PCR and the resulting DNAs are completely sequenced. These DNAs are then cloned downstream of an appropriate promoter in a vector capable of soybean transformation.

Alternatively, amiRNAs can be synthesized commercially, for example by Codon Devices, (Cambridge, Mass.). The synthesized DNA is then cloned downstream of an appropriate promoter in a vector capable of soybean transformation.

Example 5

Conversion of Genomic MicroRNA Precursors to Artificial MicroRNA Precursors

Genomic miRNA precursor genes were converted to amiRNA precursors using overlapping PCR as described in example 4 and the resulting DNAs were completely sequenced. The following nine amiRNAs precursors were made:

TABLE 4

Artificial MicroRNA Precursor Sequences

| microRNA Precursor | SEQ ID NO | Length (nucs) | Expression Construct |
|---|---|---|---|
| 156c-lox | 31 | 844 | PHP34018 |
| 159-lox | 32 | 958 | PHP32803 |
| 166b-lox | 33 | 358 | PHP34019 |
| 168c-lox | 34 | 1072 | PHP31104 |
| 398b-lox | 35 | 463 | PHP34044 |
| 159-fad2-1b | 36 | 958 | PHP32511 |
| 166b-fad2-1b | 37 | 358 | PHP32421 |
| 396b-fad2-1b | 38 | 604 | PHP32510 |
| 159-fad2-2 | 39 | 958 | see below |

SEQ IDs Nos:31-38 were then individually cloned downstream of the beta-conglycinin promoter in plasmid PHP27253 (also known as plasmid KS332, described in U.S. Patent Application No. 60/939,872, applicant's designation BB-1623 US PRV) to form expression constructs PHP34018, PHP32803, PHP34019, PHP31104, PHP34044, PHP32511, PHP32421, and PHP32510, respectively. A second amiRNA precursor, 159-fad2-2 (SEQ ID No:39) was cloned 3' (downstream) of 396b-fad2-1b (SEQ ID 38; which was cloned into PHP27253 to form PHP32510) in PHP32510 to form construct PHP32843. In a similar fashion, 159-fad2-2 was cloned 3' (downstream) of 159-fad2-1b (SEQ ID 36; PHP32511) to form construct PHP32869.

Example 6

Transformation of Soybean

Culture Conditions:

Soybean embryogenic suspension cultures (cv. Jack) are maintained in 35 mL liquid medium SB196 (infra) on a rotary shaker, 150 rpm, 26° C. with cool white fluorescent lights on 16:8 hr day/night photoperiod at light intensity of 60-85 $\mu E/m^2/s$. Cultures are subcultured every 7 days to 2 weeks by inoculating approximately 35 mg of tissue into 35 mL of fresh liquid SB196 (the preferred subculture interval is every 7 days).

Soybean embryogenic suspension cultures are transformed with soybean expression plasmids by the method of particle gun bombardment (Klein et al., *Nature,* 327:70 (1987)) using a DuPont Biolistic PDS1000/HE instrument (helium retrofit) for all transformations.

Soybean Embryogenic Suspension Culture Initiation:

Soybean cultures are initiated twice each month with 5-7 days between each initiation. Pods with immature seeds from available soybean plants 45-55 days after planting are picked, removed from their shells and placed into a sterilized magenta box. The soybean seeds are sterilized by shaking them for 15 min in a 5% Clorox solution with 1 drop of ivory soap (i.e., 95 mL of autoclaved distilled water plus 5 mL Clorox and 1 drop of soap, mixed well). Seeds are rinsed using 2 1-liter bottles of sterile distilled water and those less than 4 mm are placed on individual microscope slides. The small end of the seed is cut and the cotyledons pressed out of the seed coat. Cotyledons are transferred to plates containing SB1 medium (25-30 cotyledons per plate). Plates are wrapped with fiber tape and stored for 8 weeks. After this time secondary embryos are cut and placed into SB196 liquid media for 7 days.

Preparation of DNA for Bombardment:

Either an intact plasmid or a DNA plasmid fragment containing the delta-5 desaturase genes of interest and the selectable marker gene are used for bombardment. Fragments from soybean expression plasmids comprising the delta-5 desaturase of the present invention are obtained by gel isolation of digested plasmids. The resulting DNA fragments are separated by gel electrophoresis on 1% SeaPlaque GTG agarose (BioWhitaker Molecular Applications) and the DNA fragments containing gene cassettes are cut from the agarose gel. DNA is purified from the agarose using the GELase digesting enzyme following the manufacturer's protocol.

A 50 μL aliquot of sterile distilled water containing 3 mg of gold particles is added to 5 μL of a 1 μg/μL DNA solution (either intact plasmid or DNA fragment prepared as described above), 50 μL 2.5 M $CaCl_2$ and 20 μL of 0.1 M spermidine. The mixture is shaken 3 min on level 3 of a vortex shaker and spun for 10 sec in a bench microfuge. After a wash with 400 μL of 100% ethanol, the pellet is suspended by sonication in 40 μL of 100% ethanol. DNA suspension (5 μL) is dispensed to each flying disk of the Biolistic PDS1000/HE instrument disk. Each 5 μL aliquot contains approximately 0.375 mg gold particles per bombardment (i.e., per disk).

Tissue Preparation and Bombardment with DNA:

Approximately 150-200 mg of 7 day old embryonic suspension cultures is placed in an empty, sterile 60×15 mm petri dish and the dish is covered with plastic mesh. Tissue is bombarded 1 or 2 shots per plate with membrane rupture pressure set at 1100 PSI and the chamber is evacuated to a vacuum of 27-28 inches of mercury. Tissue is placed approximately 3.5 inches from the retaining/stopping screen.

Selection of Transformed Embryos:

Transformed embryos ate selected using hygromycin as the selectable marker. Specifically, following bombardment, the tissue is placed into fresh SB196 media and cultured as described above. Six days post-bombardment, the SB196 is exchanged with fresh SB196 containing 30 mg/L hygromycin. The selection media is refreshed weekly. Four to six weeks post-selection, green, transformed tissue is observed growing from untransformed, necrotic embryogenic clusters. Isolated, green tissue is removed and inoculated into multi-well plates to generate new, clonally propagated, transformed embryogenic suspension cultures.

Embryo Maturation:

Embryos are cultured for 4-6 weeks at 26° C. in SB196 under cool white fluorescent (Phillips cool white Econowatt F40/CW/RS/EW) and Agro (Phillips F40 Agro) bulbs (40 watt) on a 16:8 hr photoperiod with light intensity of 90-120 $\mu E/m^2 s$. After this time embryo clusters are removed to a solid agar media, SB166, for 1-2 weeks. Clusters are then subcultured to medium SB103 for 3 weeks. During this period, individual embryos are removed from the clusters and screened for alterations in their fatty acid compositions as described supra.

Media Recipes:

SB 196-FN Lite Liquid Proliferation Medium (per liter)

| | |
|---|---|
| MS FeEDTA - 100x Stock 1 | 10 mL |
| MS Sulfate - 100x Stock 2 | 10 mL |
| FN Lite Halides - 100x Stock 3 | 10 mL |
| FN Lite P, B, Mo - 100x Stock 4 | 10 mL |
| B5 vitamins (1 mL/L) | 1.0 mL |
| 2,4-D (10 mg/L final concentration) | 1.0 mL |
| $KNO_3$ | 2.83 gm |
| $(NH_4)_2SO_4$ | 0.463 gm |
| asparagine | 1.0 gm |
| sucrose (1%) | 10 gm |
| pH 5.8 | |

FN Lite Stock Solutions

| Stock Number | | 1000 mL | 500 mL |
|---|---|---|---|
| 1 | MS Fe EDTA 100x Stock | | |
| | $Na_2$ EDTA* | 3.724 g | 1.862 g |
| | $FeSO_4$—$7H_2O$ | 2.784 g | 1.392 g |
| 2 | MS Sulfate 100x stock | | |
| | $MgSO_4$—$7H_2O$ | 37.0 g | 18.5 g |
| | $MnSO_4$—$H_2O$ | 1.69 g | 0.845 g |
| | $ZnSO_4$—$7H_2O$ | 0.86 g | 0.43 g |
| | $CuSO_4$—$5H_2O$ | 0.0025 g | 0.00125 g |
| 3 | FN Lite Halides 100x Stock | | |
| | $CaCl_2$—$2H_2O$ | 30.0 g | 15.0 g |
| | KI | 0.083 g | 0.0715 g |
| | $CoCl_2$—$6H_2O$ | 0.0025 g | 0.00125 g |
| 4 | FN Lite P, B, Mo 100x Stock | | |
| | $KH_2PO_4$ | 18.5 g | 9.25 g |
| | $H_3BO_3$ | 0.62 g | 0.31 g |
| | $Na_2MoO_4$—$2H_2O$ | 0.025 g | 0.0125 g |

*Add first, dissolve in dark bottle while stirring

SB1 Solid Medium (Per Liter)

1 package MS salts (Gibco/BRL—Cat. No.11117-066)
1 mL B5 vitamins 1000× stock
31.5 g sucrose
2 mL 2,4-D (20 mg/L final concentration)
pH 5.7
8 g TC agar SB 166 Solid Medium (Per Liter)

1 package MS salts (Gibco/BRL—Cat. No.11117-066)
1 mL B5 vitamins 1000× stock
60 g maltose
750 mg $MgCl_2$ hexahydrate
5 g activated charcoal
pH 5.7
2 g gelrite SB 103 Solid Medium (Per Liter)

1 package MS salts (Gibco/BRL—Cat. No. 11117-066)
1 mL B5 vitamins 1000× stock
60 g maltose
750 mg $MgCl_2$ hexahydrate
pH 5.7
2 g gelrite SB 71-4 Solid Medium (Per Liter)

1 bottle Gamborg's B5 salts with sucrose (Gibco/ BRL—Cat. No. 21153-036)
pH 5.7
5 g TC agar 2,4-D Stock Obtain premade from Phytotech Cat. No. D 295—concentration 1 mg/mL B5 Vitamins Stock (per 100 mL)

Store aliquots at −20° C.
10 g myo-inositol
100 mg nicotinic acid
100 mg pyridoxine HCl
1 g thiamine If the solution does not dissolve quickly enough, apply a low level of heat via the hot stir plate.

Functional Analysis In Somatic Soybean Embryos

Mature somatic soybean embryos are a good model for zygotic embryos. While in the globular embryo state in liquid culture, somatic soybean embryos contain very low amounts of triacylglycerol (TAG) or storage proteins typical of maturing, zygotic soybean embryos. At this developmental stage, the ratio of total triacylglyceride to total polar lipid (phospholipids and glycolipid) is about 1:4, as is typical of zygotic soybean embryos at the developmental stage from which the somatic embryo culture was initiated. At the globular stage as well, the mRNAs for the prominent seed proteins, α'-subunit of β-conglycinin, kunitz trypsin inhibitor 3, and seed lectin are essentially absent. Upon transfer to hormone-free media to allow differentiation to the maturing somatic embryo state, TAG becomes the most abundant lipid class. As well, mRNAs for α'-subunit of β-conglycinin, kunitz trypsin inhibitor 3 and seed lectin become very abundant messages in the total mRNA population. On this basis, the somatic soybean embryo system behaves very similarly to maturing zygotic soybean embryos in vivo, and is thus a good and rapid model system for analyzing the phenotypic effects of modifying the expression of genes in the fatty acid biosynthesis pathway (see PCT Publication No. WO 2002/00904). The model system is also predictive of the fatty acid composition of seeds from plants derived from transgenic embryos.

Example 7

Assay of Lipoxygenase Phenotype and Results

Transformations of Glycine max cv. Jack were carried out with five constructs containing artificial microRNA sequences targeted against lipoxygenase sequences under the control of a seed specific promoter. The amiRNA would be expected to silence all three seed specific lipoxygenases as it has a one bp difference from the lipoxygenase 1 and lipoxygenase 3 sequences and two bp changes from the lipoxygenase 2 sequence. After transformation soybean somatic embryos were collected for use in the lipoxygenase assay.

Preparation of Soybean Somatic Embryo Extract

Somatic soybean embryos were individually ground in 500 μL of 2 mM sodium taurodeoxycholate in a microtiter plate (96 deep-well microtiter plates with a 1.2-2 mL working volume per well) using one 4 mm or 5/32" steel grinding ball per embryo. The embryos were ground with two 30-45 second cycles at 1500 strokes/min using a Geno/Grinder™ (SPEX CertiPrep, Metuchen, N.J.). The microtiter plates were then centrifuged using an Eppendorf Centrifuge 5804R with rotor A-2-MTP at 4000 rpm for 5 min to remove cellular debris.

Preparation of Soybean Bulk Seed Extract

The LOX1 enzyme assay was also to assay soybean cv Jack seeds as a positive control for lipoxygenase activity and seeds carrying the triple lox null mutation as a negative control for lipoxygenase activity. The assay on multiple seeds was carried out as follows. Seeds were placed into a Geno/Grinder™ with a 9/16-inch stainless steel ball being placed on top of the seeds. The seeds were ground using the Geno/Grinder™ at 1600 rpm for 30 seconds; additional 30-second grindings of the seeds were done until the seeds were pulverized to a homogeneous powder. A small amount (approximately 10-15 mg) of pulverized soybean powder was transferred to a 1.5 mL microfuge tube and the soybean powder was suspended, by vortexing, in 800 μL sterile filtered ddi $H_2OL$. The vials containing the samples were then inverted and allowed to sit on the bench at room temperature for approximately 2-3 minutes. Debris was compacted by centrifugation using a micro-centrifuge at top speed.

Assay for Soybean LOX1

Lipoxygenase activity was determined using a spectrophotometric assay where sodium linoleate is hydroperoxidated increasing the 234 nm absorbance of the sample. When measuring LOX1 activity in soybeans (Glycine max cv. Jack) the absorbance at 234 nm increases in 1-3 minutes to about 0.5 or 0.6 OD234nm min-1.

Sodium linoleate substrate was prepared from linoleic acid as follows. Seventy mg of linoleic acid and 70 mg of Tween 20 were weighed out into a 50 mL tube and homogenized in 4 mL sterile filtered double deionized (ddi) $H_2O$. About 0.55 mL of 0.5 N NaOH was added in order to obtain a clear solution. Sterile filtered double distilled $H_2O$ was added to bring the solution up to 25 mL total volume. The solution was divided in 2 mL aliquots which were stored at −20° C. under argon gas. The final stock concentration of sodium linoleate was 10 mM.

To measure lipoxygenase activity in soybean somatic embryos or soybean seeds 100 μL of 0.2 mM sodium linoleate (18:2) in 0.1 M sodium borate, pH 9.0 was added first to a 96-well standard UV grade microtiter plate suitable for a microtiter plate reader then 10 μL of the soybean extract was added to each well and the increase in absorbance at 234 nm was monitored for 5 minutes at a 9 second interval using a microtiter plate reader SpectraMax 190 (Molecular Devices Corp., Sunnyvale, Calif.).

The assay described in this Example was specific for the detection of LOX1. No lipoxygenase activity was observed when this assay was performed on seeds of a soybean mutant with mutations in all three seed expressed lipoxygenase genes while a high level of activity was found in cv. Jack seeds.

TABLE 5

Silencing Efficacy of amiRNAs

| construct # | amiRNA | % silencing |
|---|---|---|
| PHP34018 | 156c-lox | 0 |
| PHP32803 | 159-lox | 82 |
| PHP34019 | 166b-lox | 0 |
| PHP31104 | 168c-lox | 76 |
| PHP37825 | 396b-lox | 83 |
| PHP34044 | 398b-lox | 0 |

These results show that the amiRNA precursors are capable of producing amiRNAs that are effective in gene silencing.

Example 8

Assay of Fatty Acid Phenotype and Results

Transformations of Glycine max cv. Jack were carried out with three constructs containing artificial microRNA sequences targeted against fatty acid desaturase 2-1 under the control of a seed specific promoter. Additional transformations of Glycine max cv. Jack were carried out with two constructs containing two artificial microRNA sequences; one targeted against fatty acid desaturase 2-1 and one targeted against fatty acid desaturase 2-2 both under the control of the same seed specific promoter. Silencing of fatty acid desaturase 2-1 would be expected to lead to increased levels of oleic acid somatic embryos and seeds as compared to non-transformed seeds and somatic embryos. Silencing of fatty acid desaturase 2-1 and fatty acid desaturase 2-2 would be expected to lead to increased levels of oleic acid in somatic embryos and seeds as compared to non-transformed somatic embryos and seeds. After transformation soybean somatic embryos were collected for use in the lipoxygenase assay.

GC analysis of FAME was employed to investigate if amiRNA expression alters the fatty acid profile of soybean somatic embryos. Approximately 5 somatic embryos were analyzed per event and 25-50 events were analyzed per construct. Each somatic embryo was placed in a GC vial. For transesterification, 50 µL of trimethylsulfonium hydroxide (TMSH) was added to the GC vial and were incubated for 30 minutes at room temperature while shaking. Then 0.4 mL of heptane were added to the GC vial and incubated for 30 min at room temperature while shaking. Fatty acid methyl esters (5 µL injected from heptane layer) were separated and quantified using a Hewlett-Packard 6890 Gas Chromatograph fitted with an Omegawax 320 fused silica capillary column (Catalog #24152, Supelco Inc.). The oven temperature was programmed to hold at 220° C. for 2.6 min, increase to 240° C. at 20° C./min and then hold for an additional 2.4 min. Carrier gas was supplied by a Whatman hydrogen generator. Retention times were compared to those for methyl esters of standards commercially available (Nu-Chek Prep, Inc.). An event was considered silenced if three or more somatic embryos showed oleic acid levels greater then 20%.

TABLE 6

Silencing Efficacy of amiRNAs

| construct # | amiRNA | % silencing |
|---|---|---|
| PHP32511 | 159-fad2-1b | 26 |
| PHP32421 | 166b-fad2-1b | 0 |
| PHP37826 | 168c-fad2-1b | 0 |
| PHP32510 | 396b-fad2-1b | 30 |
| PHP32843 | 396b-fad2-1b & 159-fad2-2 | 80 |
| PHP32869 | 159-fad2-1b & 159-fad2-1b | 80 |

These results show that some of the amiRNA precursors are capable of producing amiRNAs that are effective in gene silencing.

Example 9

Generation and Analysis of Seeds with a Silenced Phenotype

Dried down embryos as described in Example 6 were germinated and plants were regenerated. Seeds from transgenic plants were harvested and assayed for lipoxygenase activity as in example 7 or fatty acid content as in example 8. The phenotypes obtained were consistent with the results obtained in the transgenic embryos (data not shown). Protein extracted from seeds from plants transformed with the lipoxygenase constructs was examined using SDS polyacrylamide gel analysis. Lipoxygenase is such an abundant protein that the band can be identified visually in stained gels using Jack (wild type control) and a mutant that does not produce seed lipoxygenase as comparators. Transgenic seeds did not have visible lipoxygenase production in agreement with the results obtained from the lipoxygenase assays (data not shown).

Transgenic seeds were also planted in the greenhouse and the plants were allowed to self-fertilize. Seeds will be collected and analyzed for lipoxygenase activity as in Example 7 or fatty acid content as in Example 8 This analysis will show that the effect of these constructs is heritable and stable.

Example 10

Constructs to Silence fad2-1 and fatB

At times it is desirable to silence more than one gene with a given construct. Individual amiRNA precursors can be operably linked to the same or different promoters. Alternatively, two or more amiRNA precursors can be operably linked to each other and then linked to one promoter. From such a construct two or more amiRNAs would be produced. Such constructs to silence fad2-1 and fad2-2 are described in Example 4 and Example 8. As an additional example, constructs were made to silence both fad2-1 and fatB. fad2-1 is described above. fatB is a thioesterase encoding a palmitoyl-thioesterase (Kinney, A. J. (1997) Genetic engineering of oilseeds for desired traits. In: Genetic Engineering, Vol. 19, (Setlow J. K. Plenum Press, New York, N.Y., pp. 149-166.). Down-regulation of fatB would result in decreased levels of saturated fatty acids, primarily a reduction in palmitate, whereas down-regulation of fad2-1 results in elevated levels of oleic acid and a reduction in polyunsaturated fatty acids.

The amiRNA, star sequence for fad2-1 described in examples 2 and 3 was used and converted into amiRNA precursors as described in Example 4. For fatB the amiRNA was designed as described in Example 2, the microRNA is 5'-ugcugcuuuucccccuuaccc-3' (the DNA sequence corresponding to this amiRNA is represented by SEQ ID NO: 40). Artificial star sequences were designed as described in Example 3 and are shown in Table 7. amiRNA precursors were created as explained in Example 4.

TABLE 7

Artificial microRNA Star Sequences

| amiRNA precursor | Star Sequence | SEQ ID NO |
|---|---|---|
| 159-fatB | gggtaagggggctaagcagcta | 41 |
| 396b-fatB | gggcaaggggaaaagcagca | 42 |

These precursors were cloned downstream of fad 2-1 precursors (described in Example 4) to create the cassettes described in Table 8. Cassettes were cloned downstream of an embryo specific promoter as previously described. Soybean transformation was performed as described in Example 6 and embryos were assayed for fatty acid phenotype as described in Example 8. No embryos showed the expected phenotype for silencing of fatB.

Examination of various ESTs encoding fatB suggests that many of the ESTs have a polyadenylation signal upstream of the sequence complementary to the fatB microRNA, thus they would not be silenced. Alternatively, it is known that the three dimensional structure of the mRNA can inhibit cleavage and thus the silencing of the gene (Long et al. (2007) Potent effect of target structure on microRNA function Nature Structural & Molecular Biology 14, 287-294. Published online: 1 Apr. 2007) and it is possible that the three dimensional structure of fatB inhibited the function of the designed amiRNA. Additional amiRNAs have been constructed and are being tested.

TABLE 8

Artificial miRNA constructs containing amiRNAs designed to silence both fad 2-1 and fatB

| PHP Number | cassette |
|---|---|
| PHP33278 | 159-fad2-1/159-fatB |
| PHP33283 | 159-fad2-1/396b-fatB |
| PHP33284 | 396b-fad2-1/159-fatB |
| PHP33285 | 396b-fad2-1/396b-fatB |

Example 11

Constructs to Silence Phosphoglucomutase (PGM)

The above examples show the silencing of the soybean fad2-1, fad2-2 and lipoxygenase genes, but it is known to those skilled in the art that amiRNAs can be constructed to silence many genes. As an example of another gene that can be silenced, an amiRNA targeting phosphoglucomutase (PGM, U.S. Pat. No. 7,323,560) was designed as described in Example 2, and the DNA sequence corresponding to these amiRNAs is shown in Table 9. Artificial star sequences were designed as described in Example 3 and are shown in Table 10. amiRNA precursors were created as explained in Example 4.

TABLE 9

Artificial microRNA Sequences

| Designation | Artificial microRNA | SEQ ID NO |
|---|---|---|
| a | ttccaaaactctcttccccgc | 43 |
| b | tcgcccatcacctcccaacac | 44 |
| c | tcccaaaaaatttccaaccag | 45 |
| d | taaacttaataccccaatcat | 46 |

TABLE 10

Artificial microRNA Star Sequences

| amiRNA precursor | Star Sequence | SEQ ID NO |
|---|---|---|
| 159-PGMa | gcggggaagaggttttggat | 47 |
| 168c-PGMb | ctgttgtgaggtgatggccga | 48 |
| 159-PGMc | ctggttggaaaccttttgggt | 49 |
| 159-PGMd | atgattggggtcataagtttt | 50 | amiRNA precursors were cloned downstream of an embryo specific promoter as previously described and constructs were transformed into soybean as described in Example 6. Transgenic soybeans in which PGM has been silenced show a phenotype of decreased starch in late stage embryos. Silencing was determined by a visual examination of embryos stained with potassium iodide. Alternatively, starch was also measured using gas chromatography. Two constructs gave gene silencing while results are pending for the remaining two constructs (Table 11).

TABLE 11

Artificial miRNA constructs silence PGM

| construct | % silencing |
|---|---|
| 159-PGMa | 22 |
| 168c-PGMb | 33 |
| 159-PGMc | not available |
| 159-PGMd | not available |

What is claimed is:

1. An isolated nucleic acid fragment encoding an artificial microRNA (amiRNA) precursor, said fragment comprising a deoxyribonucleotide sequence wherein (i) nucleotides 196 to 216 of SEQ ID NO:17 are replaced by a first variable nucleotide subsequence ranging in size from 19 to 24 nucleotides depending upon a target sequence whose expression is to be reduced, (ii) nucleotides 262 to 282 of SEQ ID NO:17 are replaced by a second variable nucleotide subsequence ranging in size from 19 to 24 nucleotides, said second variable nucleotide subsequence being capable of hybridizing to the first variable subsequence, and (iii) the amiRNA precursor produced by said isolated nucleic acid fragment has the same stem structure as the precursor miRNA produced by endogenous SEQ ID NO:17.

2. A recombinant construct comprising the isolated nucleic acid fragment of claim 1 operably linked to at least one regulatory sequence.

3. A plant cell comprising the recombinant construct of claim 2.

4. The plant cell of claim 3 wherein the plant cell is a monocot plant cell.

5. A method for reducing expression of a target sequence in a plant cell, said method comprising: (a) transforming at least one plant cell with a nucleic acid construct encoding an artificial microRNA (amiRNA) precursor, said construct comprising a deoxyribonucleotide sequence wherein (i) nucleotides 196 to 216 of SEQ ID NO:17 are replaced by a first variable nucleotide subsequence ranging in size from 19 to 24 nucleotides depending upon a target sequence whose expression is to be reduced, (ii) nucleotides 262 to 282 of SEQ ID NO:17 are replaced by a second variable nucleotide subsequence ranging in size from 19 to 24 nucleotides, said second variable nucleotide subsequence being capable of hybridizing to the first variable subsequence, and (iii) the amiRNA precursor produced by said isolated nucleic acid fragment has the same stem structure as the precursor miRNA produced by endogenous SEQ ID NO:17; and (b) selecting those transformed plant cell(s) whose level of expression of the target sequence is reduced when compared to the level of expression of the target sequence in a wild type plant cell.

6. The method of claim 5 wherein the plant cell is a monocot plant cell.

7. An artificial miRNA transcribed from the isolated nucleic acid fragment of claim 1.

* * * * *

SEQUENCE LISTING

```
<160> NUMBER OF SEQ ID NOS: 50

<210> SEQ ID NO 1
<211> LENGTH: 38
<212> TYPE: DNA
<213> ORGANISM: Artificial
<220> FEATURE:
<223> OTHER INFORMATION: primer 156cA

<400> SEQUENCE: 1
ggtacctcga gtttcatcaa agaaaataac ttctgaac                          38

<210> SEQ ID NO 2
<211> LENGTH: 36
<212> TYPE: DNA
<213> ORGANISM: Artificial
<220> FEATURE:
<223> OTHER INFORMATION: primer 156cS
```

```
<220> FEATURE:
<221> NAME/KEY: misc_feature
<222> LOCATION: (18)..(18)
<223> OTHER INFORMATION: n is a, c, g, or t

<400> SEQUENCE: 2
ggatccatgg tagaatcnta cactttggta gccctg                          36

<210> SEQ ID NO 3
<211> LENGTH: 36
<212> TYPE: DNA
<213> ORGANISM: Artificial
<220> FEATURE:
<223> OTHER INFORMATION: primer 159A

<400> SEQUENCE: 3
ggtacctcga gttctagcta gctagggttt gggtag                          36

<210> SEQ ID NO 4
<211> LENGTH: 37
<212> TYPE: DNA
<213> ORGANISM: Artificial
<220> FEATURE:
<223> OTHER INFORMATION: primer 159S

<400> SEQUENCE: 4
ggatccatgg agatttgttt ataaaaatcc aacaatc                         37

<210> SEQ ID NO 5
<211> LENGTH: 36
<212> TYPE: DNA
<213> ORGANISM: Artificial
<220> FEATURE:
<223> OTHER INFORMATION: primer 166bA

<400> SEQUENCE: 5
ggtacctcga ggtgcagatt gagagaaaga tgaaag                          36

<210> SEQ ID NO 6
<211> LENGTH: 35
<212> TYPE: DNA
<213> ORGANISM: Artificial
<220> FEATURE:
<223> OTHER INFORMATION: primer 166bS

<400> SEQUENCE: 6
ggatccatgg gggaactata aggcttcgga ccagg                           35

<210> SEQ ID NO 7
<211> LENGTH: 35
<212> TYPE: DNA
<213> ORGANISM: Artificial
<220> FEATURE:
<223> OTHER INFORMATION: primer 168cA

<400> SEQUENCE: 7
ggtacctcga ggtgctcttt ataaataacc cctcg                           35

<210> SEQ ID NO 8
<211> LENGTH: 34
<212> TYPE: DNA
<213> ORGANISM: Artificial
<220> FEATURE:
<223> OTHER INFORMATION: primer 168cS
```

```
<400> SEQUENCE: 8
ggatccatgg aattactttg acatagtagt atgc                              34

<210> SEQ ID NO 9
<211> LENGTH: 37
<212> TYPE: DNA
<213> ORGANISM: Artificial
<220> FEATURE:
<223> OTHER INFORMATION: primer 396bA

<400> SEQUENCE: 9
ggtacctcga gcttatatat aacaaagcca taaaatc                           37

<210> SEQ ID NO 10
<211> LENGTH: 34
<212> TYPE: DNA
<213> ORGANISM: Artificial
<220> FEATURE:
<223> OTHER INFORMATION: primer 396bS

<400> SEQUENCE: 10
ggatccatgg gcgagaaact ttgtatgggc atgg                              34

<210> SEQ ID NO 11
<211> LENGTH: 39
<212> TYPE: DNA
<213> ORGANISM: Artificial
<220> FEATURE:
<223> OTHER INFORMATION: primer 398bA

<400> SEQUENCE: 11
ggtacctcga gtatatttcc acaatgatgt tattcttac                         39

<210> SEQ ID NO 12
<211> LENGTH: 38
<212> TYPE: DNA
<213> ORGANISM: Artificial
<220> FEATURE:
<223> OTHER INFORMATION: primer 398bS

<400> SEQUENCE: 12
ggatccatgg gttttgctca ttcaaatgtt cttcctag                          38

<210> SEQ ID NO 13
<211> LENGTH: 847
<212> TYPE: DNA
<213> ORGANISM: Glycine max
<220> FEATURE:
<221> NAME/KEY: misc_feature
<222> LOCATION: (840)..(840)
<223> OTHER INFORMATION: n is a, c, g, or t

<400> SEQUENCE: 13
tttcatcaaa gaaaataact tctgaactgt tcaaactgat ctcatgacaa ctgaaagaac     60
atagttcgca tacaatccat ttcatcctcc gcagcataat caattgtgct accacaacaa    120
gattgacagc aacaaaggac ccttattgaa agcttcaaca agtttaagct ttaatcattg    180
gagtacacag tacacacaca aggttttgaa tccataattt cccaacaaag acataaccac    240
ttagttagct acctactccc acaagaaagg aagtgctagt gggtcctcat tttcaacaaa    300
tccatcgaga tccatttgca gcattccgtt gtaatgaagg ttggttgttt tgcatcgaa     360 aaccaatact tgaccactag gcttatctct ttccgtttct gagcatgcat actcattcac    420
agcatcaaaa tgcacagatc ctgatggaga ttgcacaggg caggtgatgc tagattgcac    480
```

```
catactcaac tctggacttt gtgattgaag tgttgacaga agatagagag cacaacctga    540
gtcaaaggat ccaggttttg catctgtaga gagctttcgg ttgctctttc cacccattga    600
tggggcgatg gtgccatgaa taggctgaca aatgggagtt cccggcattg cttcatcacc    660
actgcctact ttagggtcat tttcttgcca aagaggatgt cccttatctt gcttatgctt    720
gtcaattctg tataaaagtc gaggagaatc atgaccagat tcagctccag ttttggcagc    780
agcaggccac atgtctctca aatagggtt ggcataagcc tcagggctac caaagtgtan    840
gattcta                                                              847

<210> SEQ ID NO 14
<211> LENGTH: 958
<212> TYPE: DNA
<213> ORGANISM: Glycine max

<400> SEQUENCE: 14
ttctagctag ctagggtttg ggtagtgagt gtaataaagt tgcaaagttt ttggttaggt     60
tacgttttga ccttattatt atagttcaaa gggaaacatt aattaaaggg gattatgaag    120
tggagctcct tgaagtccaa ttgaggatct tactgggtga attgagctgc ttagctatgg    180
atcccacagt tctacccatc aataagtgct tttgtggtag tcttgtggct tccatatctg    240
gggagcttca tttgcctttta tagtattaac cttctttgga ttgaagggag ctctacaccc    300
ttctcttctt ttctctcata ataatttaaa tttgttatag actctaaact ttaaatgttt    360
tttttgaagt ttttccgttt ttctcttttg ccatgatccc gttcttgctg tggagtaacc    420
ttgtccgagg tatgtgcatg attagatcca tacttaattt gtgtgcatca cgaaggtgag    480
gttgaaatga actttgcttt tttgaccttt taggaaagtt cttttgttgc agtaatcaat    540
tttaattagt tttaattgac actattactt ttattgtcat ctttgttagt tttattgttg    600
aattgagtgc atatttccta ggaaattctc ttacctaaca ttttttatac agatctatgc    660
tcttggctct tgcccttact cttggccttg tgttggttat ttgtctacat atttattgac    720
tggtcgatga gacatgtcac aattcttggg cttatttgtt ggtctaataa aaggagtgct    780
tattgaaaga tcaagacgga gattcggttt tatataaata aactaaagat gacatattag    840
tgtgttgatg tctcttcagg ataattttg tttgaaataa tatggtaatg tcttgtctaa    900
atttgtgtac ataattctta ctgatttttt ggattgttgg atttttataa acaaatct    958

<210> SEQ ID NO 15
<211> LENGTH: 394
<212> TYPE: DNA
<213> ORGANISM: Glycine max

<400> SEQUENCE: 15
gggaactata aggcttcgga ccaggcttca ttcccctcaa aagttcttcc tttcatttgt     60
ttctacttca aacttcaaac acaagatcat gtgtgttgtg tgtggttgag aacttgacat    120
gcttcttctt cctagcttgc aaaggtgagg ttgagaggaa tgttgtctgg ctcgaggtca    180
tggaggagga ggaggagtag agtactgaga tcagtgaaag tttccaatgg aaatttaccc    240
tcttacacaa aaaaatgatt ctcggaccag gcttcattcc ccccacccaa cttttgcttt    300
ttccttaatt taaatttctt tctctccatt ttcatatctc gcatgccctt atggtaaggc    360
tttctcttcc tttcatcttt ctctcaatct gcac                                394
```

<210> SEQ ID NO 16
<211> LENGTH: 1068
<212> TYPE: DNA
<213> ORGANISM: Glycine max

<400> SEQUENCE: 16

| | | | | | |
|---|---|---|---|---|---|
| tctttataaa | taaccccctcg | ctaacccaat | cttcacccgt | tcaccacata | tagtgtgggt | 60 |
| tggggttagc | ttcgcgattc | ttatttctct | ctttaactct | ctctctctct | cgtcctcgcg | 120 |
| gatggagaga | gagaaagtaa | gagagaaaga | gcggtggttg | gtggttttgg | tttggtgaag | 180 |
| ttcgattcga | tgcgatgcga | ttgcgttggg | gattttgatt | ctctctctct | cactgtgcgg | 240 |
| tctctaattc | gcttggtgca | ggtcgggaac | cggttttcgc | gcggaatgga | ggaacggtcg | 300 |
| ccggcggcga | attggatccc | gccttgcatc | aactgaatcg | gaggccgcgg | tgaagctttg | 360 |
| cctcgttttc | cgctcagatc | tcatctccga | gattctacca | ccagtatttt | ttaaatttat | 420 |
| tttaatctct | gcttatcaga | tccgaaacgc | ttctagattt | aagtttatcg | tctctatgca | 480 |
| gaaagtgtga | tttatgcggt | agatcccgat | gcatagaatc | tacatctaag | agaaacagtt | 540 |
| ttagttaaaa | agcttctgat | gtgcttttc | cttgtttgga | ttttacttg | acctgcttcc | 600 |
| tttcattgat | taataatcaa | gctgaaattt | ttgatatttg | agaactgaaa | taaataatct | 660 |
| tggatttatt | acaataatga | atttactgta | tcggtatagg | ttaagctaat | tgaggtgatt | 720 |
| gcgattcgat | tgggaaaaaa | aaaacatttt | ttaggttttc | tgatggtttt | tgagccttgg | 780 |
| ttgaattgaa | ttgcatgcca | cggttgcaag | tgttttatgt | gatgcattcc | attgcgatgc | 840 |
| ttgtgcttat | tctggttcga | gctatttat | attgtttgat | attgctttta | gaacagaagg | 900 |
| cttcaagtct | atgaagcatt | tgtaagtgaa | ttgtgtagca | ggaattgatg | acctgtttgg | 960 |
| ggcatgattt | gagtatctgg | ctctctgtgt | aactagcttc | tagacataga | aacccaagtt | 1020 |
| aagacttgag | gatggcttca | aattgcatac | tactatgtca | aagtaatt | | 1068 |

<210> SEQ ID NO 17
<211> LENGTH: 574
<212> TYPE: DNA
<213> ORGANISM: Glycine max
<220> FEATURE:
<221> NAME/KEY: misc_feature
<222> LOCATION: (531)..(533)
<223> OTHER INFORMATION: n is a, c, g, or t

<400> SEQUENCE: 17

| | | | | | |
|---|---|---|---|---|---|
| gcgagaaact | tgtatgggc | atggttattt | ctcacttctc | accctccttt | actttcttat | 60 |
| gctaaatcct | ccttcccccta | tatctccacc | ctcaacccct | ttttctcatt | ataacttttg | 120 |
| gtgcctagat | ggtgtgtgtg | tgtgcgcgcg | agagatctga | gctcaatttt | cctctctcaa | 180 |
| gtcctggtca | tgcttttcca | cagctttctt | gaacttctta | tgcatcttat | atctctccac | 240 |
| ctccaggatt | ttaagcccta | gaagctcaag | aaagctgtgg | gagaatatgg | caattcaggc | 300 |
| ttttaattgc | tttcatttgg | taccatcact | tgcaagattt | cagagtacaa | ggtgaacaca | 360 |
| cacatcttcc | tcttcatcaa | ttctctagtt | tcatccttat | cttttcattc | acggtaactc | 420 |
| tcactacccct | ctttcatctt | ataagttata | ccgggggtgt | gatgttgatg | agtgtaaatt | 480 |
| aaatatatgt | gatctctttc | tctggaaaaa | ttttcagtgt | gatatacata | nnnatctctt | 540 |
| aatctagaga | ttttatggct | tgttatata | taag | | | 574 |

```
<210> SEQ ID NO 18
<211> LENGTH: 463
<212> TYPE: DNA
<213> ORGANISM: Glycine max

<400> SEQUENCE: 18
gttttgctca ttcaaatgtt cttcctagtc aagtccaaat ggtttatctc agaggagtgg      60
atctgagaac acaaggctgg tttgcactgc tatattatga tcgattggta taaggtgaat     120
ttactttgtg ttctcaggtc accccttga gccaacctgt tgacatatac caaacatga      180 atccttctca ctttgcttct catctttttt tatcaccaca tcttgttata atgtcttcag     240
atttcaggaa atgttgcagg ctggattgt ggatggtata gacatcaatg ttgttatttt     300
tatacttcat tttttatact ttaatttcct ctatacctca cttttattgg agaaaaaaga    360
gaatagaaaa tagtggattt ctcttctttt tttcaatcaa agggagttgt aggggaaaag    420
tttagaaaat ggcgtgtaag aataacatca ttgtggaaat ata                      463

<210> SEQ ID NO 19
<211> LENGTH: 21
<212> TYPE: DNA
<213> ORGANISM: Artificial
<220> FEATURE:
<223> OTHER INFORMATION: amiRNA targeting lipoxygenase

<400> SEQUENCE: 19
tcatcagtca tccatggaga c                                               21

<210> SEQ ID NO 20
<211> LENGTH: 21
<212> TYPE: DNA
<213> ORGANISM: Artificial
<220> FEATURE:
<223> OTHER INFORMATION: amiRNA targeting fatty acid desaturase 2-1b

<400> SEQUENCE: 20
tgagggaaaa gggttgagga a                                               21

<210> SEQ ID NO 21
<211> LENGTH: 21
<212> TYPE: DNA
<213> ORGANISM: Artificial
<220> FEATURE:
<223> OTHER INFORMATION: amiRNA targeting fatty acid desaturase 2-2

<400> SEQUENCE: 21
tccacataaa tacactctct t                                               21

<210> SEQ ID NO 22
<211> LENGTH: 21
<212> TYPE: DNA
<213> ORGANISM: Artificial
<220> FEATURE:
<223> OTHER INFORMATION: 156c-lox star sequence

<400> SEQUENCE: 22
caatccctgt tcgactgtac a                                               21

<210> SEQ ID NO 23
<211> LENGTH: 21
<212> TYPE: DNA
<213> ORGANISM: Artificial
<220> FEATURE:
<223> OTHER INFORMATION: 159-lox star sequence
```

<400> SEQUENCE: 23
gtctccatgg agaactgatg t                                              21

<210> SEQ ID NO 24
<211> LENGTH: 21
<212> TYPE: DNA
<213> ORGANISM: Artificial
<220> FEATURE:
<223> OTHER INFORMATION: 166b-lox star sequence

<400> SEQUENCE: 24
cactccattt atgactcttg a                                              21

<210> SEQ ID NO 25
<211> LENGTH: 21
<212> TYPE: DNA
<213> ORGANISM: Artificial
<220> FEATURE:
<223> OTHER INFORMATION: 168c-lox star sequence

<400> SEQUENCE: 25
ctctccctgg atgactgttg a                                              21

<210> SEQ ID NO 26
<211> LENGTH: 22
<212> TYPE: DNA
<213> ORGANISM: Artificial
<220> FEATURE:
<223> OTHER INFORMATION: 398b-lox star sequence

<400> SEQUENCE: 26
gtcgccagtg gatgactgat ga                                             22

<210> SEQ ID NO 27
<211> LENGTH: 21
<212> TYPE: DNA
<213> ORGANISM: Artificial
<220> FEATURE:
<223> OTHER INFORMATION: 159-fad2-1b star sequence

<400> SEQUENCE: 27
ttcctcaacc caattccctc t                                              21

<210> SEQ ID NO 28
<211> LENGTH: 21
<212> TYPE: DNA
<213> ORGANISM: Artificial
<220> FEATURE:
<223> OTHER INFORMATION: 166b-fad2-1b star sequence

<400> SEQUENCE: 28
cccctcaagg cttttcaatc a                                              21

<210> SEQ ID NO 29
<211> LENGTH: 21
<212> TYPE: DNA
<213> ORGANISM: Artificial
<220> FEATURE:
<223> OTHER INFORMATION: 396b-fad2-1b star sequence

<400> SEQUENCE: 29
ttactcaacc cttttccctc a                                              21

<210> SEQ ID NO 30
<211> LENGTH: 21
<212> TYPE: DNA
<213> ORGANISM: Artificial
<220> FEATURE:
<223> OTHER INFORMATION: 159-fad2-2 star sequence

<400> SEQUENCE: 30
aagagagtgt acctatgtgg t                                       21

<210> SEQ ID NO 31
<211> LENGTH: 844
<212> TYPE: DNA
<213> ORGANISM: Artificial
<220> FEATURE:
<223> OTHER INFORMATION: amiRNA precursor 156c-lox

<400> SEQUENCE: 31
tttcatcaaa gaaataact tctgaactgt tcaaactgat ctcatgacaa ctgaaagaac    60
atagttcgca tacaatccat ttcatcctcc gcagcataat caattgtgct accacaacaa   120
gattgacagc aacaaaggac ccttattgaa agcttcaaca agtttaagct ttaatcattg   180
gagtacacag tacacacaca aggttttgaa tccataattt cccaacaaag acataaccac   240
ttagttagct acctactccc acaagaaagg aagtgctagt gggtcctcat tttcaacaaa   300
tccatcgaga tccatttgca gcattccgtt gtaatgaagg ttggttgttt ttgcatcgaa   360
aaccaatact tgaccactag gctcaatccc tgttcgactg tacacatact cattcacagc   420
atcaaaatgc acagatcctg atggagattg cacagggcag gtgatgctag attgcaccat   480
actcaactct ggactttgtg attgaagtgt catcagtcat ccatggagac aacctgagtc   540
aaaggatcca ggttttgcat ctgtagagag ctttcggttg ctctttccac ccattgatgg   600
ggcgatggtg ccatgaatag gctgacaaat gggagttccc ggcattgctt catcaccact   660
gcctacttta gggtcatttt cttgccaaag aggatgtccc ttatcttgct tatgcttgtc   720
aattctgtat aaaagtcgag gagaatcatg accagattca gctccagttt tggcagcagc   780
aggccacatg tctctcataa tagggttggc ataagcctca gggctaccaa agtgtaggat   840
tcta                                                               844

<210> SEQ ID NO 32
<211> LENGTH: 958
<212> TYPE: DNA
<213> ORGANISM: Artificial
<220> FEATURE:
<223> OTHER INFORMATION: amiRNA precursor 159-lox

<400> SEQUENCE: 32
ttctagctag ctagggtttg ggtagtgagt gtaataaagt tgcaaagttt ttggttaggt    60
tacgttttga cctttattatt atagttcaaa gggaaacatt aattaaaggg gattatgaag   120
gtctccatgg agaactgatg ttgaggatct tactgggtga attgagctgc ttagctatgg   180
atcccacagt tctacccatc aataagtgct tttgtggtag tcttgtggct tccatatctg   240
gggagcttca tttgcctttta tagtattaac cttctcatca gtcatccatg gagaccaccc   300
ttctcttctt ttctctcata ataatttaaa tttgttatag actctaaact ttaaatgttt   360
tttttgaagt ttttccgttt ttctcttttg ccatgatccc gttcttgctg tggagtaacc   420
ttgtccgagg tatgtgcatg attagatcca tacttaattt gtgtgcatca cgaaggtgag   480
gttgaaatga actttgcttt tttgaccttt taggaaagtt cttttgttgc agtaatcaat   540

| | |
|---|---|
| tttaattagt tttaattgac actattactt ttattgtcat ctttgttagt tttattgttg | 600 |
| aattgagtgc atatttccta ggaaattctc ttacctaaca ttttttatac agatctatgc | 660 |
| tcttggctct tgcccttact cttggccttg tgttggttat ttgtctacat atttattgac | 720 |
| tggtcgatga gacatgtcac aattcttggg cttatttgtt ggtctaataa aaggagtgct | 780 |
| tattgaaaga tcaagacgga gattcggttt tatataaata aactaaagat gacatattag | 840 |
| tgtgttgatg tctcttcagg ataatttttg tttgaaataa tatggtaatg tcttgtctaa | 900 |
| atttgtgtac ataattctta ctgattttt ggattgttgg attttataa acaaatct | 958 |

<210> SEQ ID NO 33
<211> LENGTH: 358
<212> TYPE: DNA
<213> ORGANISM: Artificial
<220> FEATURE:
<223> OTHER INFORMATION: amiRNA precursor 166b-lox

<400> SEQUENCE: 33

| | |
|---|---|
| tcaaaagttc ttcctttcat ttgtttctac ttcaaacttc aaacacaaga tcatgtgtgt | 60 |
| tgtgtgtggt tgagaacttg acatgcttct tcttcctagc ttgcaaaggt gaggttgaca | 120 |
| ctccatttat gactcttgag gtcatggagg aggaggagga gtagagtact gagatcagtg | 180 |
| aaagtttcca atggaaattt accctcttac acaaaaaaat gattctcatc agtcatccat | 240 |
| ggagacccac ccaacttttg cttttttcctt aatttaaatt tctttctctc cattttcata | 300 |
| tctcgcatgc ccttatggta aggctttctc ttcctttcat ctttctctca atctgcac | 358 |

<210> SEQ ID NO 34
<211> LENGTH: 1072
<212> TYPE: DNA
<213> ORGANISM: Artificial
<220> FEATURE:
<223> OTHER INFORMATION: amiRNA precursor 168c-lox

<400> SEQUENCE: 34

| | |
|---|---|
| gtgatcttta taaataaccc ctcgctaacc caatcttcac ccgttcacca catatagtgt | 60 |
| gggtaggggt tagcttcgcg attcttattt ctctctttaa ctctctctct ctctcgtcct | 120 |
| cgcggatgga gagagagaaa gtaagagaga aagagcggtg gttggtggtt ttggtttggt | 180 |
| gaagttcgat tcgatgcgat gcgattgcgt tggggatttt gattctctct ctctcactgt | 240 |
| gcggtctcta attcatcagt catccatgga gacccggttt tcgcgcggaa tggaggaacg | 300 |
| gtcgccggcg ccgaattggc tctccctgga tgactgttga atcggaggcc gcggtgaacc | 360 |
| tttgcctcgt tttccgctca gatctcatct ccgagattct accaccagta ttttttaaat | 420 |
| ttattttaat ctctgcttat cagatccgaa acgcttctag atttaagttt atcgtctcta | 480 |
| tgcagaaagt gtgatttatg cggtagatcc cgatgcatag aatctacatc taagagaaac | 540 |
| agttttagtt aaaaagcttc tgatgtgctt tttccttgtt tggattttta cttgacctgc | 600 |
| ttcctttcat tgattaataa tcaagctgaa attttgata tttgagaact gaaataaata | 660 |
| atcttggatt tattacaata atgaatttac tgtatcggta taggttaagc taattgaggt | 720 |
| gattgcgatt cgattgggaa aaaaaaaaca ttttttaggt ttttctgatgg tttttgagcc | 780 |
| ttggttgaat tgaattgcat gccacggttg caagtgtttt atgtgatgca ttccattgcg | 840 |
| atgcttgtgc ttattctggt tcgagctatt ttatattgtt tgatattgct tttagaacag | 900 |
| aaggcttcaa gtctatgaag catttgtaag tgaattgtgt agcaggaatt gatgacctgt | 960 |

```
ttggggcatg atttgagtat ctggctctct gtgtaactag cttctagaca tagaaaccca      1020
agttaagact tgaggatggc ttcatattgc atactactat gtcaaagtaa tt              1072

<210> SEQ ID NO 35
<211> LENGTH: 463
<212> TYPE: DNA
<213> ORGANISM: Artificial
<220> FEATURE:
<223> OTHER INFORMATION: amiRNA precursor 398b-lox

<400> SEQUENCE: 35
ttttgctcat tcaaatgttc ttcctagtca agtccaaatg gtttatctca ggtcgccagt        60
ggatgactga tgaaggctgg tttgcactgc tatattatga tcgattggta taaggtgaat       120
ttactttcat cagtcatcca tggagactga gccaacctgt tgacatatac caaaacatga       180
atccttctca ctttgcttct catcttttt tatcaccaca tcttgttata atgtcttcag        240
atttcaggaa atgttgcagg ctggatttgt ggatggtata gacatcaatg ttgttatttt       300
tatacttcat tttttatact ttaatttcct ctatacctca cttttattgg agaaaaaaga       360
gaatagaaaa tagtggattt ctcttctttt tttcaatcaa agggagttgt aggggaaaag       420
tttagaaaat ggcgtgtaag aataacatca ttgtggaaat ata                        463

<210> SEQ ID NO 36
<211> LENGTH: 958
<212> TYPE: DNA
<213> ORGANISM: Artificial
<220> FEATURE:
<223> OTHER INFORMATION: amiRNA precursor 159-fad2-1b

<400> SEQUENCE: 36
ttctagctag ctagggtttg ggtagtgagt gtaataaagt tgcaaagttt ttggttaggt        60
tacgttttga ccttattatt atagttcaaa gggaaacatt aattaaaggg gattatgaag       120
ttcctcaacc caattccctc ttgaggatct tactgggtga attgagctgc ttagctatgg       180
atcccacagt tctacccatc aataagtgct tttgtggtag tcttgtggct tccatatctg       240
gggagcttca tttgccttta tagtattaac cttctgaggg aaaagggttg aggaacaccc       300
ttctcttctt ttctctcata ataatttaaa tttgttatag actctaaact ttaaatgttt       360
tttttgaagt ttttccgttt ttctctttg ccatgatccc gttcttgctg tggagtaacc        420
ttgtccgagg tatgtgcatg attagatcca tacttaattt gtgtgcatca cgaaggtgag       480
gttgaaatga actttgcttt tttgaccttt taggaaagtt cttttgttgc agtaatcaat       540
tttaattagt tttaattgac actattactt ttattgtcat ctttgttagt tttattgttg       600
aattgagtgc atatttccta ggaaattctc ttacctaaca ttttttatac agatctatgc       660
tcttggctct tgcccttact cttggccttg tgttggttat ttgtctacat atttattgac       720
tggtcgatga gacatgtcac aattcttggg cttatttgtt ggtctaataa aaggagtgct       780
tattgaaaga tcaagacgga gattcggttt tatataaata aactaaagat gacatattag       840
tgtgttgatg tctcttcagg ataatttttg tttgaaataa tatggtaatg tcttgtctaa       900
atttgtgtac ataattctta ctgattttttt ggattgttgg attttataa acaaatct        958

<210> SEQ ID NO 37
<211> LENGTH: 358
<212> TYPE: DNA
<213> ORGANISM: Artificial
<220> FEATURE:
<223> OTHER INFORMATION: amiRNA precursor 166b-fad2-1b
```

<400> SEQUENCE: 37

```
tcaaaagttc ttcctttcat ttgtttctac ttcaaacttc aaacacaaga tcatgtgtgt    60
tgtgtgtggt tgagaacttg acatgcttct tcttcctagc ttgcaaaggt gaggttgacc   120
cctcaaggct tttcaatcag gtcatggagg aggaggagga gtagagtact gagatcagtg   180
aaagtttcca atggaaattt accctcttac acaaaaaaat gattctgagg gaaaagggtt   240
gaggaaccac ccaacttttg cttttttcctt aatttaaatt tctttctctc cattttcata   300
tctcgcatgc ccttatggta aggctttctc ttcctttcat ctttctctca atctgcac     358
```

<210> SEQ ID NO 38
<211> LENGTH: 604
<212> TYPE: DNA
<213> ORGANISM: Artificial
<220> FEATURE:
<223> OTHER INFORMATION: amiRNA precursor 396b-fad2-1b

<400> SEQUENCE: 38

```
gcgagaaact tgtatgggc atggttattt ctcacttctc accctccttt actttcttat    60
gctaaatcct ccttccccta tatctccacc ctcaacccct ttttctcatt ataacttttg   120
gtgcctagat ggtgtgtgtg tgtgcgcgcg agagatctga gctcaatttt cctctctcaa   180
gtcctggtca tgctttgagg gaaaagggtt gaggaactta tgcatcttat atctctccac   240
ctccaggatt ttaagcccta gttactcaac cctttttccct cagaatatgg caattcaggc   300
ttttaattgc tttcatttgg taccatcact tgcaagattt cagagtacaa ggtgaacaca   360
cacatcttcc tcttcatcaa ttctctagtt tcatccttat cttttcattc acggtaactc   420
tcactaccct ctttcatctt ataagttata ccggggtgt gatgttgatg agtgtaaatt   480
aaatatatgt gatctctttc tctggaaaaa ttttcagtgt gatatacata ataatctctt   540
aatctagaga ttttatggct tgttatata taagcggcca attctgcaga tatccatcac   600
actg                                                                604
```

<210> SEQ ID NO 39
<211> LENGTH: 958
<212> TYPE: DNA
<213> ORGANISM: Artificial
<220> FEATURE:
<223> OTHER INFORMATION: amiRNA precursor 159-fad2-2

<400> SEQUENCE: 39

```
ttctagctag ctagggtttg ggtagtgagt gtaataaagt tgcaaagttt ttggttaggt    60
tacgttttga ccttattatt atagttcaaa gggaaacatt aattaaaggg gattatgaag   120
aagagagtgt acctatgtgg ttgaggatct tactgggtga attgagctgc ttagctatgg   180
atcccacagt tctacccatc aataagtgct tttgtggtag tcttgtggct tccatatctg   240
gggagcttca tttgcctta tagtattaac cttctccaca taaatacact ctcttcaccc   300
ttctcttctt ttctctcata ataatttaaa tttgttatag actctaaact ttaaatgttt   360
ttttgaagt ttttccgttt ttctcttttg ccatgatccc gttcttgctg tggagtaacc   420
ttgtccgagg tatgtgcatg attagatcca tacttaattt gtgtgcatca cgaaggtgag   480
gttgaaatga actttgcttt tttgaccttt taggaaagtt cttttgttgc agtaatcaat   540
tttaattagt tttaattgac actattactt ttattgtcat ctttgttagt tttattgttg   600
aattgagtgc atatttccta ggaaattctc ttacctaaca ttttttatac agatctatgc   660
tcttggctct tgcccttact cttggccttg tgttggttat ttgtctacat atttattgac   720
```

```
tggtcgatga gacatgtcac aattcttggg cttatttgtt ggtctaataa aaggagtgct    780
tattgaaaga tcaagacgga gattcggttt tatataaata aactaaagat gacatattag    840
tgtgttgatg tctcttcagg ataattttg tttgaaataa tatggtaatg tcttgtctaa     900
atttgtgtac ataattctta ctgatttttt ggattgttgg attttataa acaaatct       958
```

```
<210> SEQ ID NO 40
<211> LENGTH: 21
<212> TYPE: DNA
<213> ORGANISM: Artificial
<220> FEATURE:
<223> OTHER INFORMATION: amiRNA targeting fatB

<400> SEQUENCE: 40
tgctgctttt cccccttacc c                                               21

<210> SEQ ID NO 41
<211> LENGTH: 22
<212> TYPE: DNA
<213> ORGANISM: Artificial
<220> FEATURE:
<223> OTHER INFORMATION: 159-fatB star sequence

<400> SEQUENCE: 41
gggtaagggg gctaagcagc ta                                              22

<210> SEQ ID NO 42
<211> LENGTH: 22
<212> TYPE: DNA
<213> ORGANISM: Artificial
<220> FEATURE:
<223> OTHER INFORMATION: 396b-fatB star sequence

<400> SEQUENCE: 42
gggtaagggg gctaagcagc ta                                              22

<210> SEQ ID NO 43
<211> LENGTH: 21
<212> TYPE: DNA
<213> ORGANISM: Artificial
<220> FEATURE:
<223> OTHER INFORMATION: amiRNA targeting PGMa

<400> SEQUENCE: 43
ttccaaaact ctcttccccg c                                               21

<210> SEQ ID NO 44
<211> LENGTH: 21
<212> TYPE: DNA
<213> ORGANISM: Artificial
<220> FEATURE:
<223> OTHER INFORMATION: amiRNA targeting PGMb

<400> SEQUENCE: 44
tcgcccatca cctcccaaca c                                               21

<210> SEQ ID NO 45
<211> LENGTH: 21
<212> TYPE: DNA
<213> ORGANISM: Artificial
<220> FEATURE:
<223> OTHER INFORMATION: amiRNA targeting PGMc

<400> SEQUENCE: 45
tcccaaaaaa tttccaacca g                                               21
```

```
<210> SEQ ID NO 46
<211> LENGTH: 21
<212> TYPE: DNA
<213> ORGANISM: Artificial
<220> FEATURE:
<223> OTHER INFORMATION: amiRNA targeting PGMd

<400> SEQUENCE: 46
taaacttaat accccaatca t                                          21

<210> SEQ ID NO 47
<211> LENGTH: 21
<212> TYPE: DNA
<213> ORGANISM: Artificial
<220> FEATURE:
<223> OTHER INFORMATION: 159-PGMa star sequence

<400> SEQUENCE: 47
gcggggaaga ggtttttgga t                                          21

<210> SEQ ID NO 48
<211> LENGTH: 21
<212> TYPE: DNA
<213> ORGANISM: Artificial
<220> FEATURE:
<223> OTHER INFORMATION: 168c-PGMb star sequence

<400> SEQUENCE: 48
ctgttgtgag gtgatggccg a                                          21

<210> SEQ ID NO 49
<211> LENGTH: 21
<212> TYPE: DNA
<213> ORGANISM: Artificial
<220> FEATURE:
<223> OTHER INFORMATION: 159-PGMc star sequence

<400> SEQUENCE: 49
ctggttggaa acctttggg t                                           21

<210> SEQ ID NO 50
<211> LENGTH: 21
<212> TYPE: DNA
<213> ORGANISM: Artificial
<220> FEATURE:
<223> OTHER INFORMATION: 159-PGMd star sequence

<400> SEQUENCE: 50
atgattgggg tcataagttt t                                          21
```